(12) United States Patent
Shin et al.

(10) Patent No.: US 12,424,731 B2
(45) Date of Patent: Sep. 23, 2025

(54) WEARABLE DEVICE INCLUDING ANTENNA

(71) Applicant: Samsung Electronics Co., Ltd., Suwon-si (KR)

(72) Inventors: Yongjoo Shin, Suwon-si (KR); Donguk Choi, Suwon-si (KR); Minhwa Hong, Suwon-si (KR); Sohyeon Kim, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 281 days.

(21) Appl. No.: 18/174,227

(22) Filed: Feb. 24, 2023

(65) Prior Publication Data
US 2023/0238684 A1 Jul. 27, 2023

Related U.S. Application Data

(63) Continuation of application No. PCT/KR2023/001036, filed on Jan. 20, 2023.

(30) Foreign Application Priority Data

Jan. 24, 2022 (KR) .................. 10-2022-0010194
Apr. 1, 2022 (KR) .................. 10-2022-0041366

(51) Int. Cl.
*H01Q 1/22* (2006.01)
*H01Q 1/27* (2006.01)
*H01Q 9/04* (2006.01)

(52) U.S. Cl.
CPC .......... *H01Q 1/2291* (2013.01); *H01Q 1/273* (2013.01); *H01Q 9/0407* (2013.01)

(58) Field of Classification Search
CPC .... H01Q 1/2291; H01Q 1/273; H01Q 9/0407; H01Q 21/28
See application file for complete search history.

(56) References Cited

U.S. PATENT DOCUMENTS 11,005,193 B2  5/2021  Kim et al.
11,025,761 B1  6/2021  Shim et al.
(Continued)

FOREIGN PATENT DOCUMENTS

CN   110277629 A   9/2019
CN   215299495 U   12/2021
(Continued)

OTHER PUBLICATIONS

International Search Report dated May 3, 2023, issued in International Application No. PCT/KR2023/001036.
(Continued)

*Primary Examiner* — Hai V Tran
(74) *Attorney, Agent, or Firm* — Jefferson IP Law, LLP

(57) ABSTRACT

A wearable device is provided. The wearable device includes a housing, an input member disposed on a lateral surface of the housing and including an outer lateral surface including a conductive portion and a non-conductive portion, a metal member disposed inside the housing and in contact with the conductive portion of the outer lateral surface, a printed circuit board (PCB) disposed on the metal member, a patch antenna including a conductive patch disposed on a surface of the PCB facing the input member at a location corresponding to the non-conductive portion, a wireless communication circuit electrically connected to the PCB and the patch antenna, and a processor connected to the metal member. The wireless communication circuit transmits a signal by feeding power to the patch antenna, and the processor acquires user biometric information through the metal member and the conductive portion of the input member.

20 Claims, 20 Drawing Sheets

(56) References Cited

U.S. PATENT DOCUMENTS

| | | | |
|---|---|---|---|
| 11,271,304 B2 | 3/2022 | Yoo et al. | |
| 11,276,926 B2* | 3/2022 | Yun | H01Q 1/243 |
| 2017/0025747 A1 | 1/2017 | Vanjani et al. | |
| 2017/0133752 A1 | 5/2017 | Choi et al. | |
| 2019/0072912 A1 | 3/2019 | Pandya et al. | |
| 2020/0073339 A1 | 3/2020 | Roach et al. | |
| 2020/0259251 A1* | 8/2020 | Seo | H01Q 15/08 |
| 2020/0329550 A1* | 10/2020 | Seo | H05K 1/0203 |
| 2020/0358203 A1* | 11/2020 | Park | H01Q 21/08 |
| 2021/0000364 A1 | 1/2021 | Lee et al. | |
| 2021/0159599 A1 | 5/2021 | Park et al. | |
| 2021/0210869 A1* | 7/2021 | Lee | H01Q 1/38 |
| 2021/0344106 A1 | 11/2021 | Sung et al. | |
| 2022/0216594 A1* | 7/2022 | Song | H01Q 15/24 |

FOREIGN PATENT DOCUMENTS

| | | |
|---|---|---|
| KR | 10-2010-0048273 A | 5/2010 |
| KR | 10-2017-0053385 A | 5/2017 |
| KR | 10-2018-0024336 A | 3/2018 |
| KR | 10-2019-0092097 A | 8/2019 |
| KR | 10-2021-0021657 A | 3/2021 |
| KR | 10-2021-0046211 A | 4/2021 |

OTHER PUBLICATIONS

Extended European Search Report dated Mar. 12, 2025, issued in European Patent Application No. 23743539.1.

\* cited by examiner

WEARABLE DEVICE INCLUDING ANTENNA

CROSS-REFERENCE TO RELATED APPLICATION(S)

This application is a continuation application, claiming priority under § 365(c), of an International application No. PCT/KR2023/001036, filed on Jan. 20, 2023, which is based on and claims the benefit of a Korean patent application number 10-2022-0010194, filed on Jan. 24, 2022, in the Korean Intellectual Property Office, and of a Korean patent application number 10-2022-0041366, filed on Apr. 1, 2022, in the Korean Intellectual Property Office, the disclosure of each of which is incorporated by reference herein in its entirety.

TECHNICAL FIELD

The disclosure relates to a wearable device including an antenna.

BACKGROUND ART

In line with the high degree of integration of electronic devices and the widespread use of super-fast and/or large-capacity wireless communication, it has recently become possible to equip a single electronic device (for example, mobile communication terminal) with various functions. For example, not only a communication function, but also an entertainment function (for example, gaming), a multimedia function (for example, music/video playback), communication and security functions for mobile banking and the like, a scheduling function, or a health service (for example, healthcare) may be integrated into a single electronic device.

In connection with communication functions of electronic devices, there have been efforts to develop 5$^{th}$ generation (5G) communication systems or pre-5G communication systems to satisfy wireless data traffic demands that have been increasing since commercialization of 4$^{th}$ generation (4G) communication systems. In order to accomplish higher data transmission rates, it has been considered to implement 5G communication systems in high-frequency (millimeter wave (mmWave)) bands (for example, 20 gigahertz (GHz) to about 300 GHz). In addition, in order to alleviate free-space loss in mmWave bands and to increase radio wave propagation distances, there has been discussion on technologies, in next-generation communication systems (for example, 5G communication systems), regarding beam-forming, massive multi-input multi-output (MIMO), full dimensional MIMO (FD-MIMO), array antennas, analog beam-forming, or large scale-antennas.

Some electronic devices have become compact and/or lightweight to be able to operate even when worn on the body of users. Such electronic devices operating while being worn on human bodies may acquire users' biometric information and may provide additional information based on the biometric information (health care function). Users' biometric information acquired through electronic devices may include not only the body temperature and/or the heartrate, but also electrocardiogram (ECG) or bioelectrical impedance analysis (BIA).

The above information is presented as background information only to assist with an understanding of the disclosure. No determination has been made, and no assertion is made, as to whether any of the above might be applicable as prior art with regard to the disclosure.

DISCLOSURE

Technical Problem

In connection with disposing an antenna module supporting an mmWave band inside a wearable device (for example, smart watch), the space to mount the antenna module and other electronic components may be insufficient due to the relative insufficient inner space inherent in the structure of the wearable device.

In addition, in connection with disposing an antenna module supporting an mmWave band inside a wearable device, the antenna radiation performance may be degraded by a metal material (for example, housing of the wearable device) existing in the area in which the antenna module radiates radio frequency (RF) signals.

In addition, if at least a part of the area in which the antenna module radiates RF signals is replaced with a nonconductive material, the performance of the function for acquiring the user's biometric information through the metal material may be degraded.

Aspects of the disclosure are to address at least the above-mentioned problems and/or disadvantages and to provide at least the advantages described below. Accordingly, an aspect of the disclosure is to provide a wearable device including an antenna configured to radiate signals in mmWave bands through at least a part of an input member of the wearable device.

Additional aspects will be set forth in part in the description which follows and, in part, will be apparent from the description, or may be learned by practice of the presented embodiments.

Technical Solution

In accordance with an aspect of the disclosure, a wearable device is provided. The wearable device includes a housing including a first surface, a second surface facing a direction opposite to the first surface, and a lateral surface surrounding a space between the first surface and the second surface, a first input member disposed on the lateral surface of the housing and including a first outer lateral surface including a first conductive portion and at least one first non-conductive portion, a first metal member disposed inside the housing and in contact with at least a portion of the first conductive portion of the first outer lateral surface, a first printed circuit board (PCB) disposed on the first metal member, a first patch antenna including at least one conductive patch disposed on a first surface of the first PCB facing the first input member to be arranged at a location corresponding to the at least one first non-conductive portion, a wireless communication circuit electrically connected to the first PCB and the first patch antenna, and at least one processor electrically connected to the first metal member, wherein the wireless communication circuit transmits a signal of a first frequency band by feeding power to the first antenna array, and the at least one processor acquires user biometric information through the first metal member and the first conductive portion of the first input member.

In accordance with another aspect of the disclosure, an electronic device is provided. The electronic device includes a housing including a first surface, a second surface facing a direction opposite to the first surface, and a lateral surface surrounding a space between the first surface and the second surface, a first input member disposed on the lateral surface of the housing and including a first outer lateral surface including a first conductive portion and at least one first non-conductive portion, a second input member disposed on the lateral surface of the housing to be spaced apart from the first input member and including a second outer lateral surface including a second conductive portion and at least one second non-conductive portion, a first PCB disposed inside the housing to face the first outer lateral surface, a second PCB disposed inside the housing to face the second outer lateral surface, at least one first conductive patch disposed on a first surface of the first PCB facing the at least one first non-conductive portion of the first outer lateral surface, at least one second conductive patch disposed on a second surface of the second PCB facing the at least one second non-conductive portion of the second outer lateral surface, and a wireless communication circuit electrically connected to the first PCB and the second PCB, wherein the wireless communication circuit transmits a signal of a first frequency band by feeding power to at least a portion of the at least one first conductive patch or the at least one second conductive patch.

Advantageous Effects

According to various embodiments disclosed herein, an antenna module including a patch antenna may be positioned to correspond to an input member of a wearable device, thereby improving the inner space efficiency of the wearable device.

In addition, according to various embodiments, at least a part of the input member of the wearable device may be made of a nonconductive material, thereby reducing degradation in the radiation performance of the patch antenna positioned to correspond to the input member.

In addition, according to various embodiments, a metal member disposed adjacent to the input member and the patch antenna may be used to acquire the user's biometric information and to radiate heat generated by the patch antenna.

Other aspects, advantages, and salient features of the disclosure will become apparent to those skilled in the art from the following detailed description, which, taken in conjunction with the annexed drawings, discloses various embodiments of the disclosure.

DESCRIPTION OF DRAWINGS

The above and other aspects, features, and advantages of certain embodiments of the disclosure will be more apparent from the following description taken in conjunction with the accompanying drawings, in which.

Throughout the drawings, it should be noted that like reference numbers are be used to depict the same or similar elements, features, and structures.

MODE FOR INVENTION

The following description with reference to the accompanying drawings is provided to assist in a comprehensive understanding of various embodiments of the disclosure as defined by the claims and their equivalents. It includes various specific details to assist in that understanding but these are to be regarded as merely exemplary. Accordingly, those of ordinary skill in the art will recognize that various changes and modifications of the various embodiments described herein can be made without departing from the scope and spirit of the disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the disclosure. Accordingly, it should be apparent to those skilled in the art that the following description of various embodiments of the disclosure is provided for illustration purpose only and not for the purpose of limiting the disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

Figure 1:
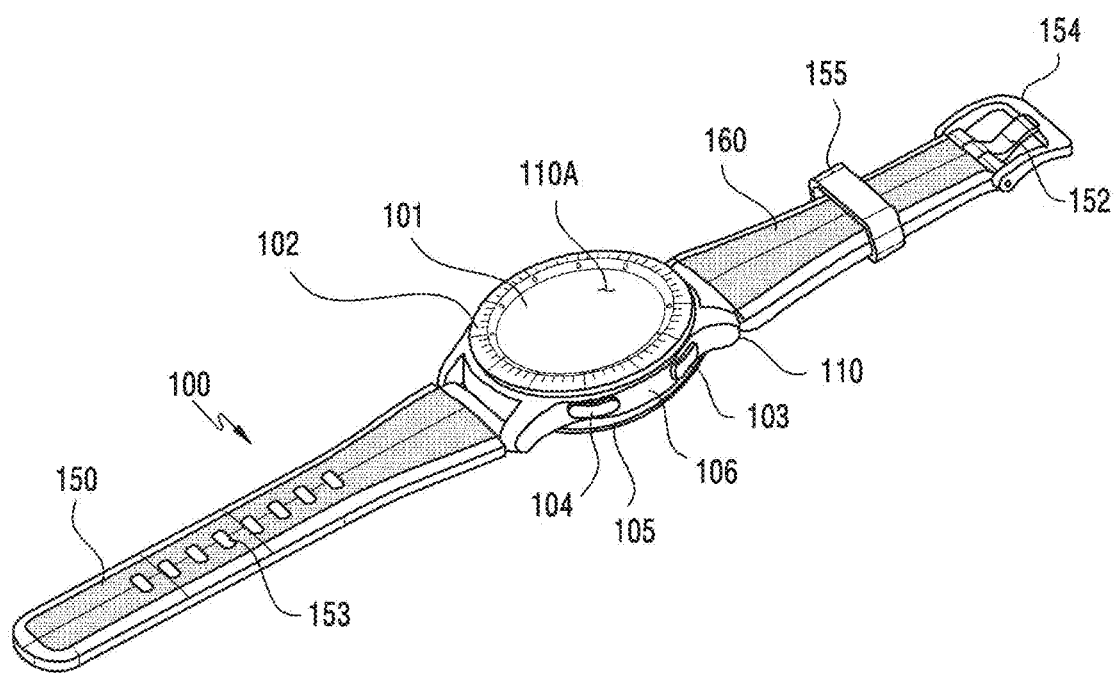
FIG. 1 is a front perspective view of a mobile electronic device according to an embodiment of the disclosure.
Figure 2:
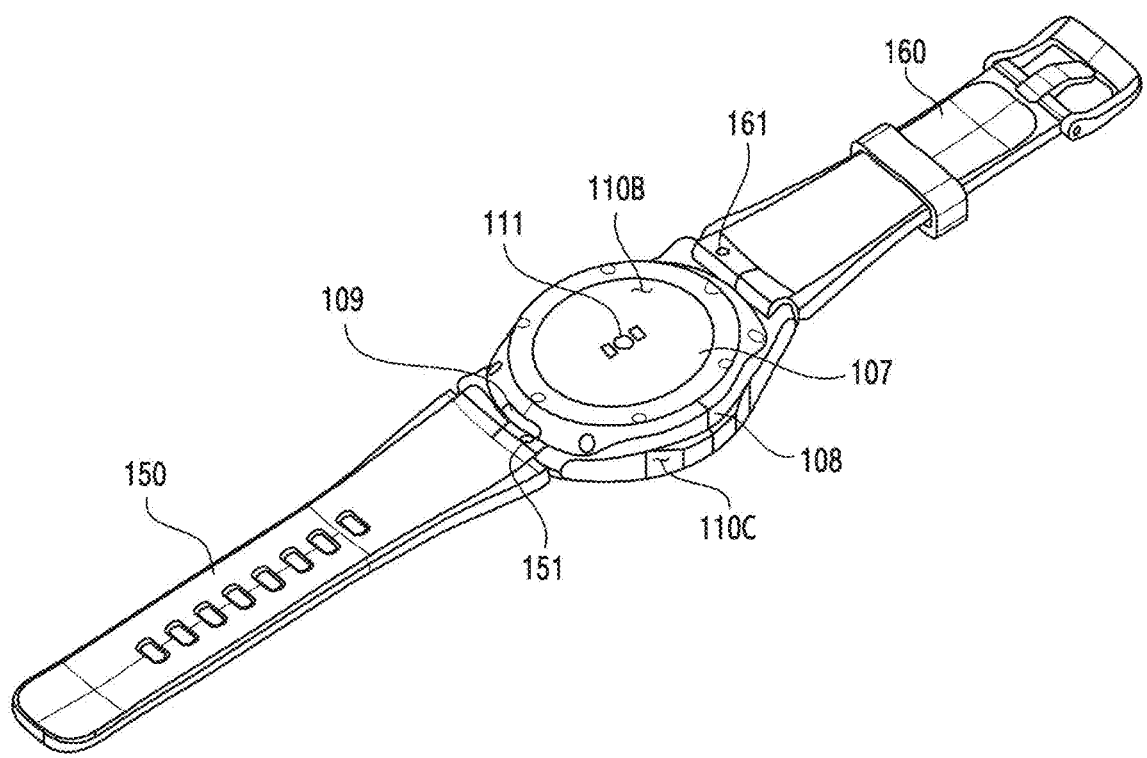
FIG. 2 is a rear perspective view of the electronic device of FIG. 1 according to an embodiment of the disclosure.
Figure 3:
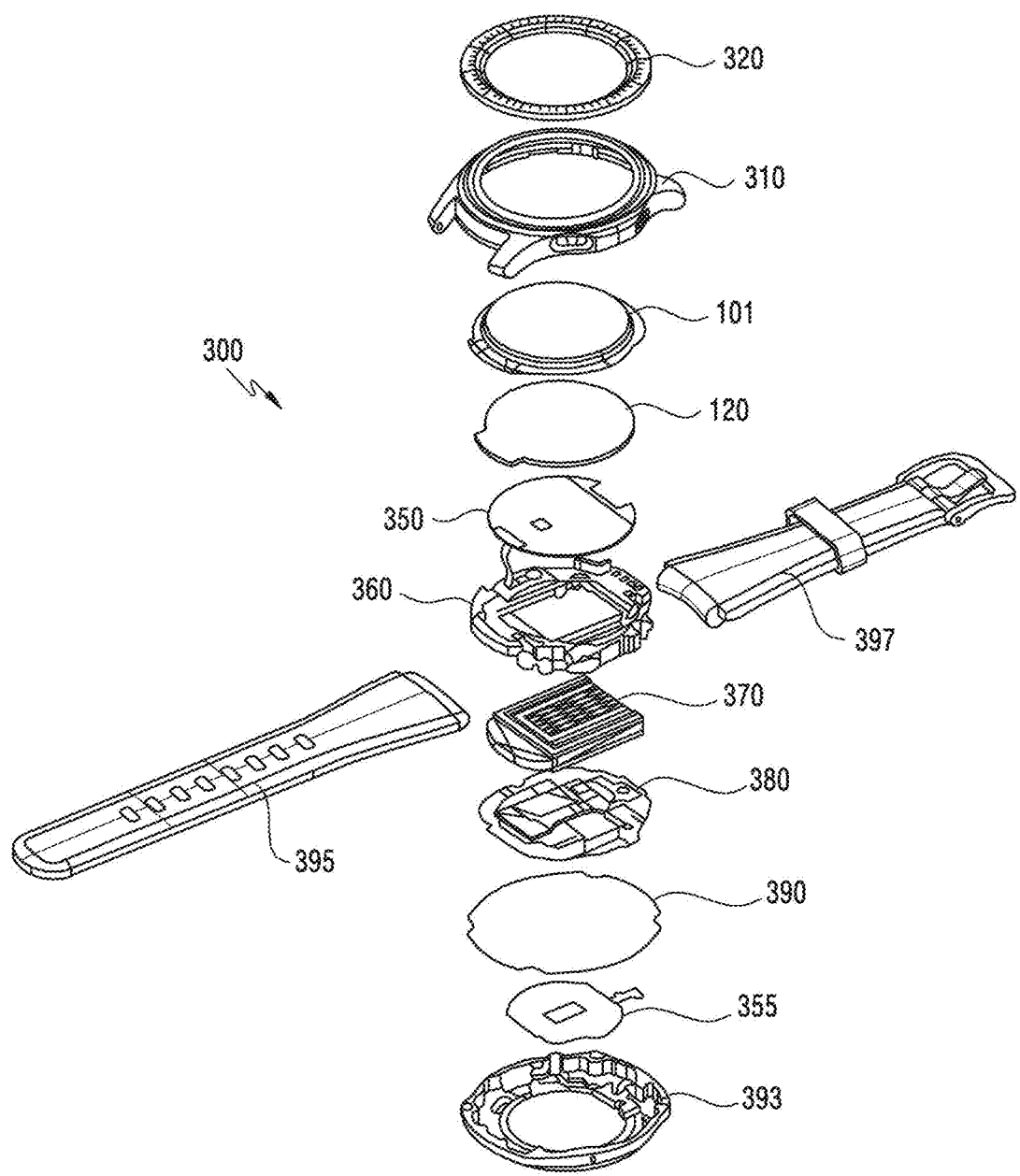
FIG. 3 is an exploded perspective view of the electronic device of FIG. 1 according to an embodiment of the disclosure.

FIG. 1 is a front perspective view of a mobile electronic device according to an embodiment of the disclosure. FIG. 2 is a rear perspective view of the electronic device of FIG. 1 according to an embodiment of the disclosure. FIG. 3 is an exploded perspective view of the electronic device of FIG. 1 according to an embodiment of the disclosure.

Referring to FIGS. 1 and 2, an electronic device 100 (or a wearable electronic device 100) according to an embodiment may include a housing 110 which includes a first surface (or a front surface) 110A, a second surface (or a rear surface) 110B, and a side surface 110C surrounding a space between the first surface 110A and the second surface 110B, and fastening members 150 and 160 connected to at least a part of the housing 110 and detachably fastening the electronic device 100 to a user's body part (e.g., a wrist, an ankle, etc.). In another embodiment (not shown), the housing may indicate a structure which forms part of the first surface 110A, the second surface 110B and the side surface 110C of FIG. 1. According to an embodiment, the first surface 110A may be formed by a front plate 101 (e.g., a glass plate including various coating layers, or a polymer plate) which is at least in part substantially transparent. The second surface 110B may be formed by a rear plate 107 which is substantially opaque. The rear plate 107 may be formed by, for example, coated or colored glass, ceramic, polymer, metal (e.g., aluminum, stainless steel (STS), or magnesium), or a combination of at least two of the above materials. The side surface 110C may be formed by a side bezel structure (or a side member) 106 which couples the front plate 101 and the rear plate 107, and includes a metal and/or a polymer. In some embodiment, the rear plate 107 and the side bezel structure 106 may be integrally formed and include the same material (e.g., a metal material such as aluminum). The fastening members 150 and 160 may be formed of various materials in various shapes. An integral link or a plurality of unit links may be formed to move with respect to each other using fabric, leather, rubber, urethane, metal, ceramic, or a combination of at least two of them.

According to an embodiment, the electronic device 100 may include at least one or more of a display 120 (see FIG. 3), audio modules 105 and 108, a sensor module 111, key input devices 102, 103, and 104 and a connector hole 109. In some embodiment, the electronic device 100 may exclude at least one (e.g., the key input devices 102, 103, and 104, the connector hole 109, or the sensor module 111) of the components or may further include other component.

The display 120 may be exposed through, for example, a considerable portion of the front plate 101. The display 120 may have a shape corresponding to a shape of the front plate 101, in various shapes such as a circle, an ellipse, or a polygon. The display 120 may be coupled with or disposed close to a touch detection circuit, a pressure sensor for measuring a touch level (pressure), and/or a fingerprint sensor.

The audio modules 105 and 108 may include a microphone hole 105 and a speaker hole 108. The microphone hole 105 may include a microphone therein to acquire an external sound, and may include a plurality of microphones therein to detect a direction of a sound in some embodiment. The speaker hole 108 may be used as an external speaker and a telephone call receiver. In some embodiment, the speaker hole 108 and the microphone hole 105 may be implemented as a single hole, or a speaker (e.g., a piezoelectric speaker) may be included without the speaker hole 108.

The sensor module 111 may generate an electric signal or a data value corresponding to an internal operating state or an external environment state of the electronic device 100. The sensor module 111 may include, for example, a biometric sensor module 111 (e.g., a heart rate monitor (HRM) sensor) disposed on the second surface 110B of the housing 110. The electronic device 100 may further include a sensor module not shown, for example, at least one of a gesture sensor, a gyro sensor, an atmospheric pressure sensor, a magnetic sensor, an acceleration sensor, a grip sensor, a color sensor, an infrared (IR) sensor, a biometric sensor, a temperature sensor, a humidity sensor, or a luminance sensor.

The key input devices 102, 103, and 104 may include a wheel key 102 disposed on the first surface 110A of the housing 110 and rotating in at least one direction, and/or side key buttons 102 and 103 disposed on the side surface 110C of the housing 110. The wheel key 102 may have a shape corresponding to the shape of the front plate 101. In another embodiment, the electronic device 100 may not include some or all of the above-mentioned key input devices 102, 103, and 104, and the key input devices 102, 103, and 104 not included may be implemented on the display 120 in other type such as soft keys. The connector hole 109 may include another connector hole (not shown) which receives a connector (e.g., a universal serial bus (USB) connector) for transmitting and receiving power and/or data to and from an external electronic device, and receives a connector for transmitting and receiving an audio signal to and from the external electronic device. The electronic device 100 may further include, for example, a connector cover (not shown) for covering at least part of the connector hole 109 and blocking inflow of an external foreign substance into the connector hole.

The fastening members 150 and 160 may be detachably fastened in at least some area of the housing 110 by using locking members 151 and 161. The fastening members 150 and 160 may include one or more of a fixing member 152, a fixing member engaging hole 153, a band guide member 154, and a band fixing ring 155.

The fixing member 152 may be configured to fix the housing 110 and the fastening members 150 and 160 to the user's body part (e.g., a wrist or an ankle). The fixing member engaging hole 153 may correspond to the fixing member 152 and secure the housing 110 and the fastening members 150 and 160 to the user's body part. The band guide member 154 may be configured to limit a movement range of the fixing member 152 if the fixing member 152 is engaged with the fixing member engaging hole 153, and thus closely fasten the fastening members 150 and 160 to the user's body part.

The band fixing ring 155 may limit the movement range of the fastening members 150 and 160, while the fixing member 152 and the fixing member fastening hole 153 are engaged.

Referring to FIG. 3, an electronic device 300 may include a side bezel structure 310, a wheel key 320, a front plate 101, a display 120, a first antenna 350, a second antenna 355, a support member 360 (e.g., a bracket), a battery 370, a printed circuit board (PCB) 380, a sealing member 390, a rear plate 393, and fastening members 395 and 397. At least one of the components of the electronic device 300 may be identical or similar to at least one of the components of the electronic device 100 of FIG. 1 or FIG. 2, and redundant descriptions thereof will be omitted herein. The support member 360 may be disposed inside the electronic device 300. The support member 360 may be connected to the side bezel structure 310, or may be integrated with the side bezel structure 310. The support member 360 may be formed of, for example, a metal material and/or a nonmetal material (e.g., a polymer). The support member 360 may be coupled with the display 120 in one surface and coupled with the PCB 380 in the other surface. A processor, a memory, and/or an interface may be mounted on the PCB 380. The processor may include, for example, at least one of a central processing unit, an application processor, a graphic processing unit (GPU), an application processor sensor processor, and a communication processor.

The memory may include, for example, a volatile memory or a nonvolatile memory. The interface may include, for example, a high definition multimedia interface (HDMI), a USB interface, a secure digital (SD) card interface, and/or an audio interface. The interface may electrically or physically connect, for example, the electronic device 300 with an external electronic device, and may include a USB connector, an SD card/multimedia card (MMC) connector, or an audio connector.

The battery 370 is a device for supplying power to at least one component of the electronic device 300, and may include, for example, a primary cell which is not rechargeable, a secondary battery which is rechargeable, or a fuel cell. At least part of the battery 370 may be substantially flushed with, for example, the PCB 380. The battery 370 may be integrally disposed inside the electronic device 300, and may be attached to and/or detached from the electronic device 300.

The first antenna 350 may be interposed between the display 120 and the support member 360. The first antenna 350 may include, for example, a near field communication (NFC) antenna, a wireless charging antenna, and/or a magnetic secure transmission (MST) antenna. The first antenna 350 may, for example, perform short-range communication with an external device or wirelessly transmit and receive power for the charging, and transmit a magnetic-based signal including a short-range communication signal or payment data. In another embodiment, an antenna structure may be formed by part or a combination of the side bezel structure 310 and/or the support member 360.

The second antenna 355 may be interposed between the PCB 380 and the rear plate 393. The second antenna 355 may include, for example, a near field communication (NFC) antenna, a wireless charging antenna, and/or a magnetic secure transmission (MST) antenna. The second antenna 355 may, for example, perform short-range communication with an external device or wirelessly transmit and receive power for the charging, and transmit a magnetic-based signal including a short-range communication signal or payment data. In another embodiment, an antenna structure may be formed by part or a combination of the side bezel structure 310 and/or the rear plate 393.

The sealing member 390 may be interposed between the side bezel structure 310 and the rear plate 393. The sealing member 390 may be configured to block moisture and foreign substance introduced from outside to the space surrounded by the side bezel structure 310 and the rear plate 393.

Figure 4A:
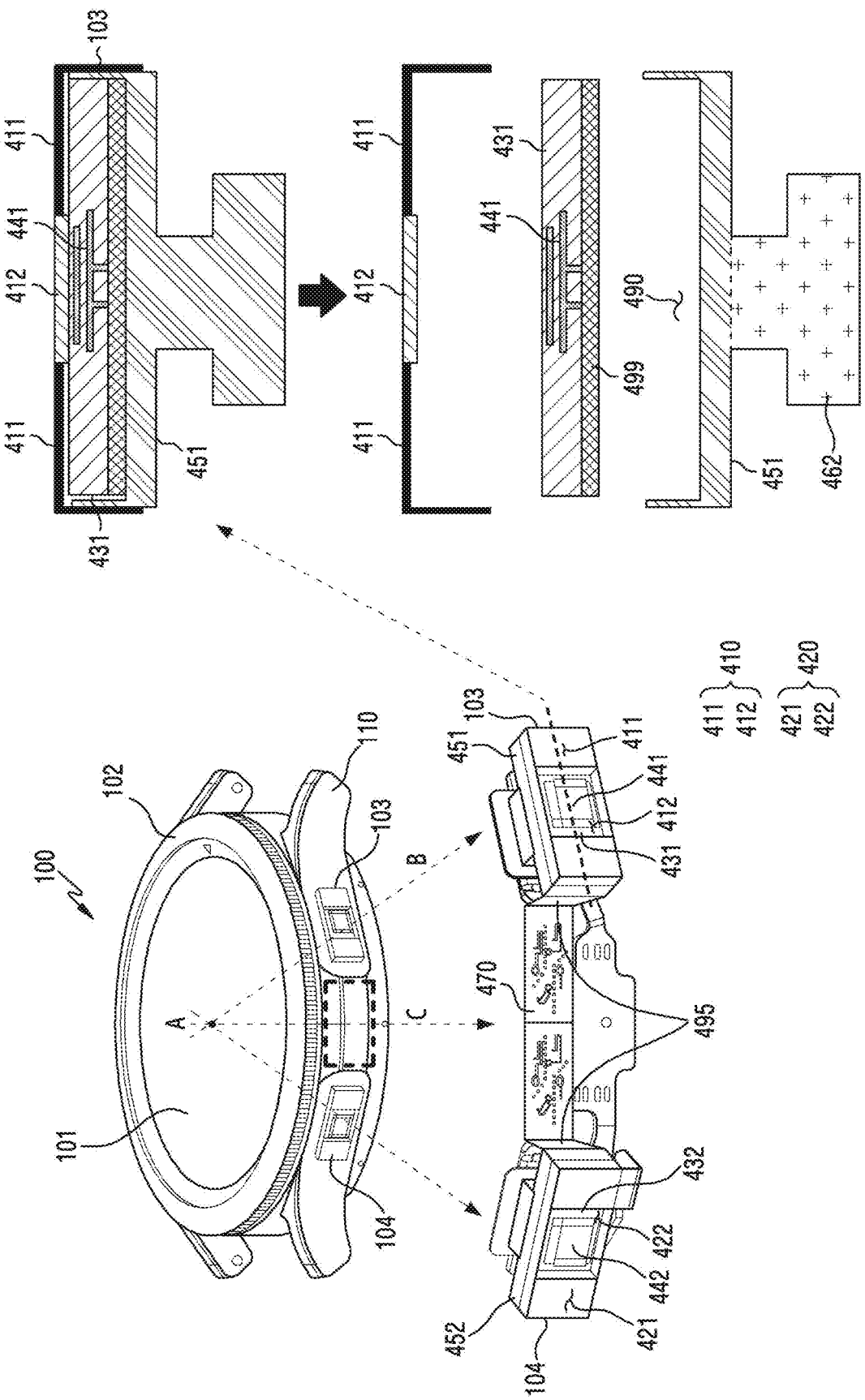
FIG. 4A illustrates a wearable device including an input member and a patch antenna according to an embodiment of the disclosure.
Figure 4B:
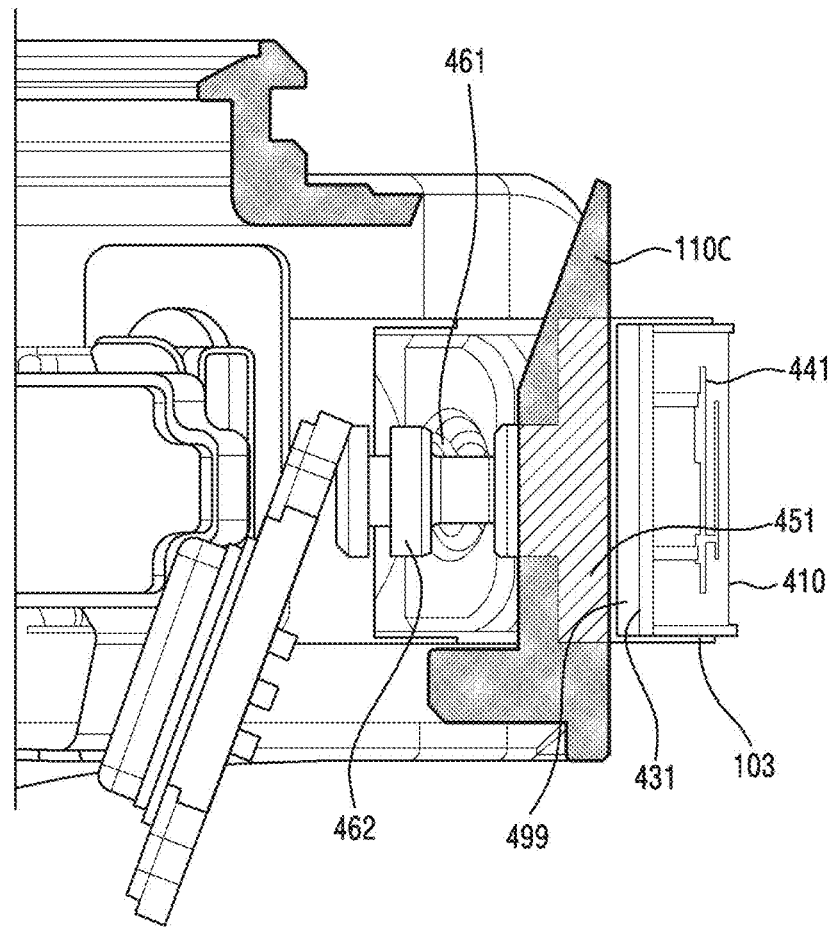
FIG. 4B is a cross-sectional view taken along axis A-B of the wearable device of FIG. 4A according to an embodiment of the disclosure.
Figure 4C:
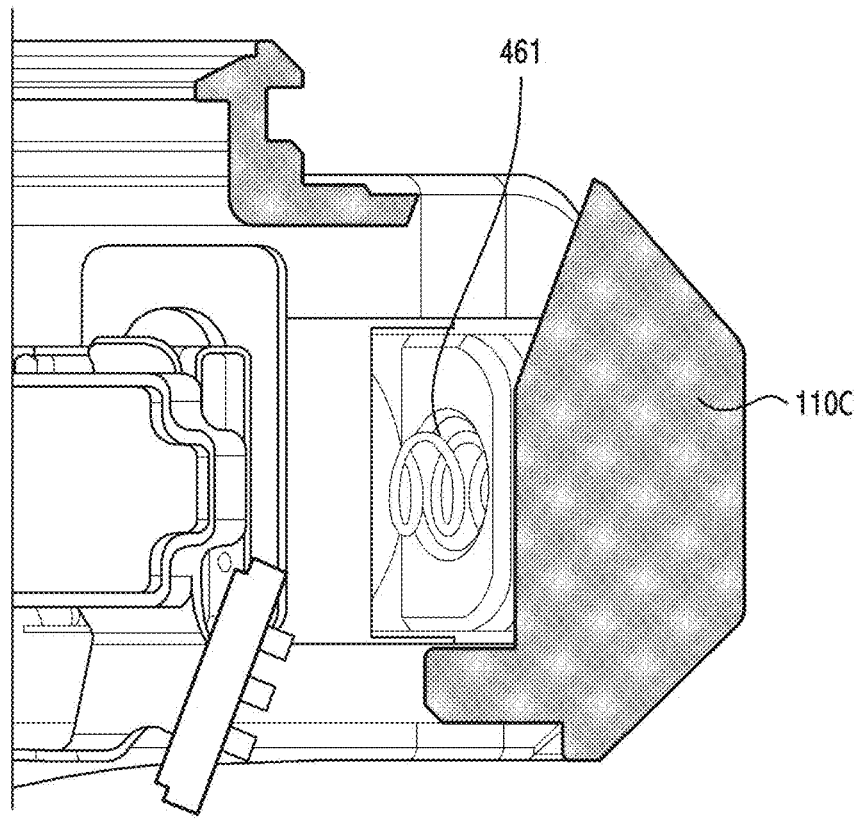
FIG. 4C is a cross-sectional view taken along axis A-C of the wearable device of FIG. 4A according to an embodiment of the disclosure.

FIG. 4A illustrates a wearable device including an input member and a patch antenna according to an embodiment of the disclosure. FIG. 4B is a cross-sectional view taken along axis A-B of the wearable device of FIG. 4A according to an embodiment of the disclosure. FIG. 4C is a cross-sectional view taken along axis A-C of the wearable device of FIG. 4A according to an embodiment of the disclosure.

Referring to FIG. 4A, the wearable device 100 (e.g., the electronic device 100 of FIGS. 1 and 2) according to an embodiment may include an input member 103 or 104 (e.g., a key input device 103 or 104 of FIGS. 1 and 2) and a conductive patch 441 or 442 disposed to face the input member 103 or 104. The same reference numerals are used for the same or substantially the same components as those described above, and overlapping descriptions will be omitted.

According to an embodiment, the wearable device 100 may include a first input member 103 disposed on the lateral surface 110C of the housing 110. According to an embodiment, the wearable device 100 may include the first input member 103 and a second input member 104 disposed on the lateral surface 110C of the housing 110. The second input member 104 according to an embodiment may be disposed to be spaced apart from the first input member 103.

Referring to FIGS. 4B and 4C together, the first input member 103 and the second input member 104 according to an embodiment may be formed in a physical button shape. For example, the housing 110 may include at least one opening formed through the lateral surface 110C, and the first input member 103 and the second input member 104 may be formed as buttons that are inserted and retracted through the opening. For example, since the wearable device 100 may include an elastic member 461 therein to provide elasticity to at least a portion of each of the first input member 103 and the second input member 104 inserted into the housing by a user input, so as to make the first input member 103 and the second input member 104 protrude out of the housing 110. For example, the first input member 103 may include a dome key 462, and may sense a user's input by receiving a pressure through the dome key 462. For another example, the first input member 103 may include a dome key 462, and the elastic member 461 may provide elasticity to the dome key 462 to make at least a portion of the first input member 103 (or the first outer lateral surface 410) protrude out of the housing 110. The second input member 104 may be formed substantially similar to the first input member 103.

According to another embodiment, each of the first input member 103 and the second input member 104 may include an electrode to be formed in a soft key shape configured to receive a touch input. However, the shapes of the first input member 103 and the second input member 104 are not limited to the above-described example, and may sense the user's input in various ways.

According to an embodiment, the first input member 103 may include a first outer lateral surface 410 including a first conductive portion 411 and a first non-conductive portion 412. According to an embodiment, at least a portion of the first outer lateral surface 410 of the first input member 103 may be exposed out of the housing 110. According to an embodiment, the second input member 104 may include a second outer lateral surface 420 including a second conductive portion 421 and a second non-conductive portion 422. According to an embodiment, at least a portion of the second outer lateral surface 420 of the second input member 104 may be exposed out of the housing 110.

According to an embodiment, the first conductive portion 411 may be used as an electrode.

According to an embodiment, the first non-conductive portion 412 may be disposed to be aligned with the first PCB 431 (or antenna module) to protect the first PCB 431. According to an embodiment, the first non-conductive portion 412 may be disposed to be aligned with the first PCB 431 to be utilized as an RF window opening through which a radio frequency (RF) signal in a designated frequency band can pass. For example, the designated frequency band may be about 3 GHz or more.

According to an embodiment, the wearable device 100 may include a first metal member 451 and/or a second metal member 452 disposed inside the housing 110. According to an embodiment, the first metal member 451 may contact at least a portion of the first conductive portion 411 of the first input member 103. According to an embodiment, the second metal member 452 may contact at least a portion of the second conductive portion 421 of the second input member 104. According to an embodiment, the first metal member 451 may operate as a part of an electrode by being in contact with the first conductive portion 411.

According to an embodiment, the at least one processor disposed inside the housing 110 of the wearable device 100 may acquire user biometric information (e.g., electrocardiogram (ECG) and/or bioelectrical impedance analysis (BIA)) through the first conductive portion 411 of the first input member 103 and the first metal member 451. For example, the at least one processor may acquire the user biometric information by applying a minute current to the first conductive portion 411 and the first metal member 451 and measuring the amount of change in the current according to a user's input. According to an embodiment, the at least one processor disposed inside the housing 110 of the wearable device 100 may acquire user biometric information (e.g., ECG and/or BIA) through the second conductive portion 421 of the second input member 104 and the second metal member 452. For example, the at least one processor may acquire user biometric information (e.g., BIA) by applying a minute current to the second conductive portion 421 and the second metal member 452 and measuring the amount of change in current according to a user's input.

According to an embodiment, the wearable device 100 may include a first PCB 431 disposed on the first metal member 451. According to an embodiment, the wearable device 100 may include a second PCB 432 disposed on the second metal member 452.

The first PCB 431 and/or the second PCB 432 according to an embodiment may be included in a mmWave antenna module configured to transmits and receive an RF signal of a mmWave band. The first PCB 431 according to an embodiment may include an antenna layer (e.g., the first conductive patch 441) including a radiator, a ground layer, and a wiring layer 499. According to an embodiment, the first metal member 451 may include a first recess 490 formed on one surface thereof. According to an embodiment, the first metal member 451 may include the first recess 490 formed on one surface thereof facing the first outer lateral surface 410 of the first input member 103. According to an embodiment, the first PCB 431 may be disposed on the first recess 490 of the first metal member 451. According to an embodiment, the second PCB 432 may be disposed on the second recess formed in the second metal member 452.

According to an embodiment, the first metal member 451 may be coupled to the first PCB 431 to fix the first PCB 431.

According to an embodiment, the first metal member 451 may be coupled to the first PCB 431 to operate as a heat sink of the first PCB 431.

According to an embodiment, the wearable device 100 may include a first conductive patch 441 disposed on one surface of the first PCB 431 toward the first input member 103. According to an embodiment, the wearable device 100 may include, on the first PCB 431, a first patch antenna including the first conductive patch 441 disposed at a location (or a region) corresponding to the first non-conductive portion 412. According to an embodiment, the first conductive patch 441 (or the first patch antenna) may be arranged to overlap at least a portion of the first non-conductive portion 412 of the first outer lateral surface 410 when viewed from the center of the housing 110.

According to an embodiment, the wearable device 100 may include a second conductive patch 442 disposed on one surface of the second PCB 432 toward the second input member 104. According to an embodiment, the wearable device 100 may include, on the second PCB 432, a second patch antenna including the second conductive patch 442 disposed at a location (or a region) corresponding to the second non-conductive portion 422. According to an embodiment, the second conductive patch 442 (or the second patch antenna) may be arranged to overlap at least a portion of the second non-conductive portion 422 of the second outer lateral surface 420 when viewed from the center of the housing 110.

According to an embodiment, the wearable device 100 may include a wireless communication circuit 470 disposed inside the housing 110. According to an embodiment, the wireless communication circuit 470 may be disposed between the first input member 103 and the second input member 104 inside the housing 110. According to an embodiment, the wireless communication circuit 470 may be disposed inside the housing 110 to be spaced apart from the first input member 103 and the second input member 104 by a substantially equal distance. According to an embodiment, the wireless communication circuit 470 may be disposed inside the housing 110 to be adjacent to the lateral surface 110C of the housing 110 at a location spaced apart from the first input member 103 and the second input member 104 by a substantially equal distance.

Figure 11:
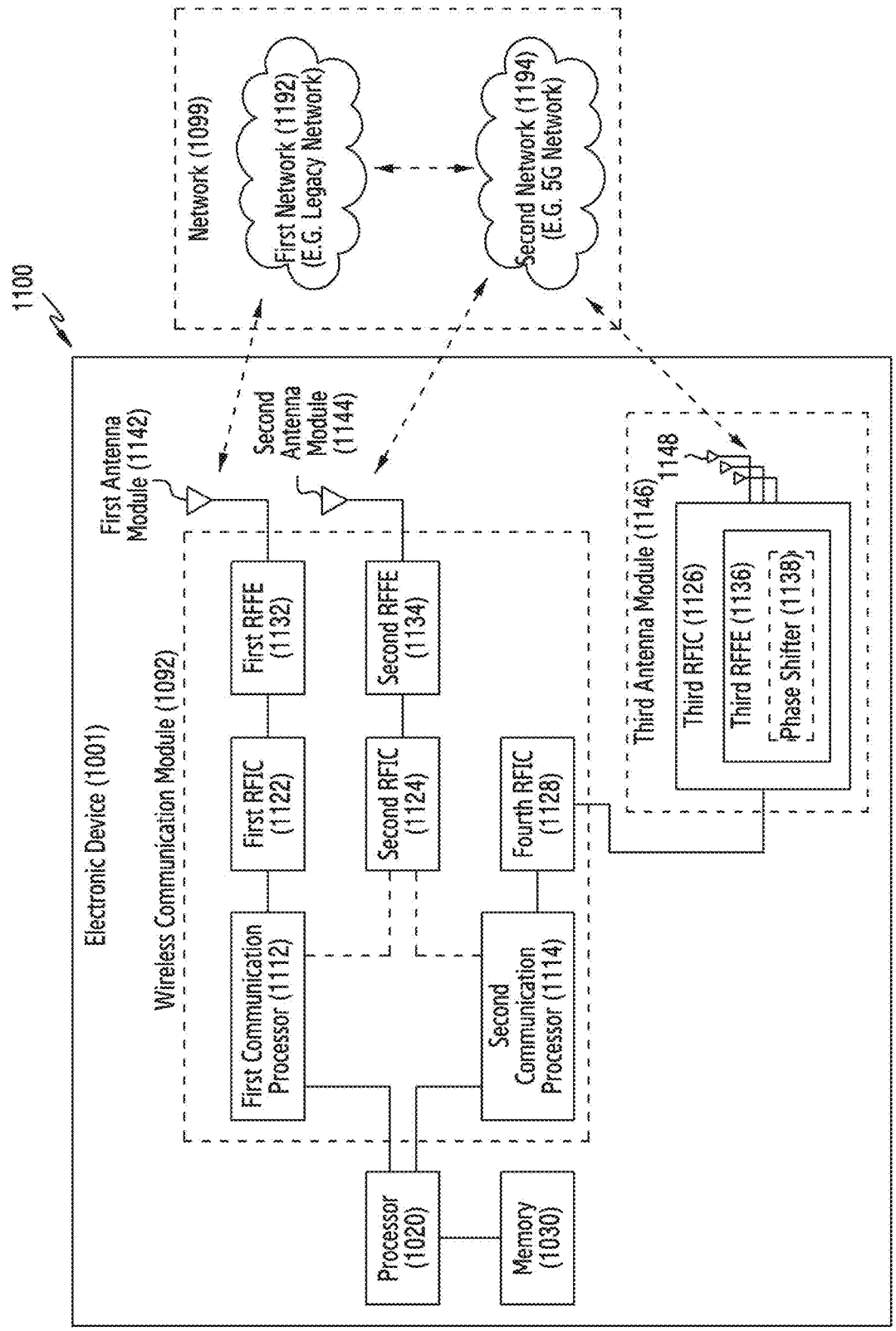
FIG. 11 is a block diagram of an electronic device for supporting legacy network communication and $5^{th}$ generation (5G) network communication according to an embodiment of the disclosure.

According to an embodiment, the wireless communication circuit 470 may include a power management integrated circuit (PMIC) and a radio frequency integrated circuit (RFIC) (e.g., the fourth RFIC 1228 of FIG. 11).

According to an embodiment, the wireless communication circuit 470 may be electrically connected to the first PCB 431 and/or the second PCB 432 through a conductive connection member 495. According to an embodiment, the wireless communication circuit 470 may be electrically connected to the first conductive patch 441 and/or the second conductive patch 442 through the conductive connection member 495. In this case, the conductive connection member 495 may be referred to as a flexible RF cable (FRC), but is not limited thereto.

According to an embodiment, the wiring layer 499 included in the first PCB 431 may be configured to be connected to the wireless communication circuit 470 so as to transmit the signal transmitted from the wireless communication circuit 470 to the first conductive patch 441 (or, the antenna layer).

According to an embodiment, the wireless communication circuit 470 may transmit and/or receive a signal of a first frequency band (e.g., mmWave band) by using the first conductive patch 441 and/or the second conductive patch 442. For example, the wireless communication circuit 470 may transmit a signal of about 28 GHz band by feeding power to the first conductive patch 441. For example, the wireless communication circuit 470 may transmit a signal of about 28 GHz band in a direction toward the first non-conductive portion 412 by feeding power to the first conductive patch 441. For example, the wireless communication circuit 470 may radiate a signal of about 28 GHz band in a direction toward the second non-conductive portion 422 by feeding power to the second conductive patch 442.

According to an embodiment, while the at least one processor acquires user biometric information (e.g., electrocardiogram) by using the first conductive portion 411 and the first metal member 451 or the second conductive portion 421 and the second metal member 452, the wireless communication circuit 470 may transmit and/or receive a signal of the first frequency band by feeding power to the first conductive patch 441 and/or the second conductive patch 442.

Figure 5A:
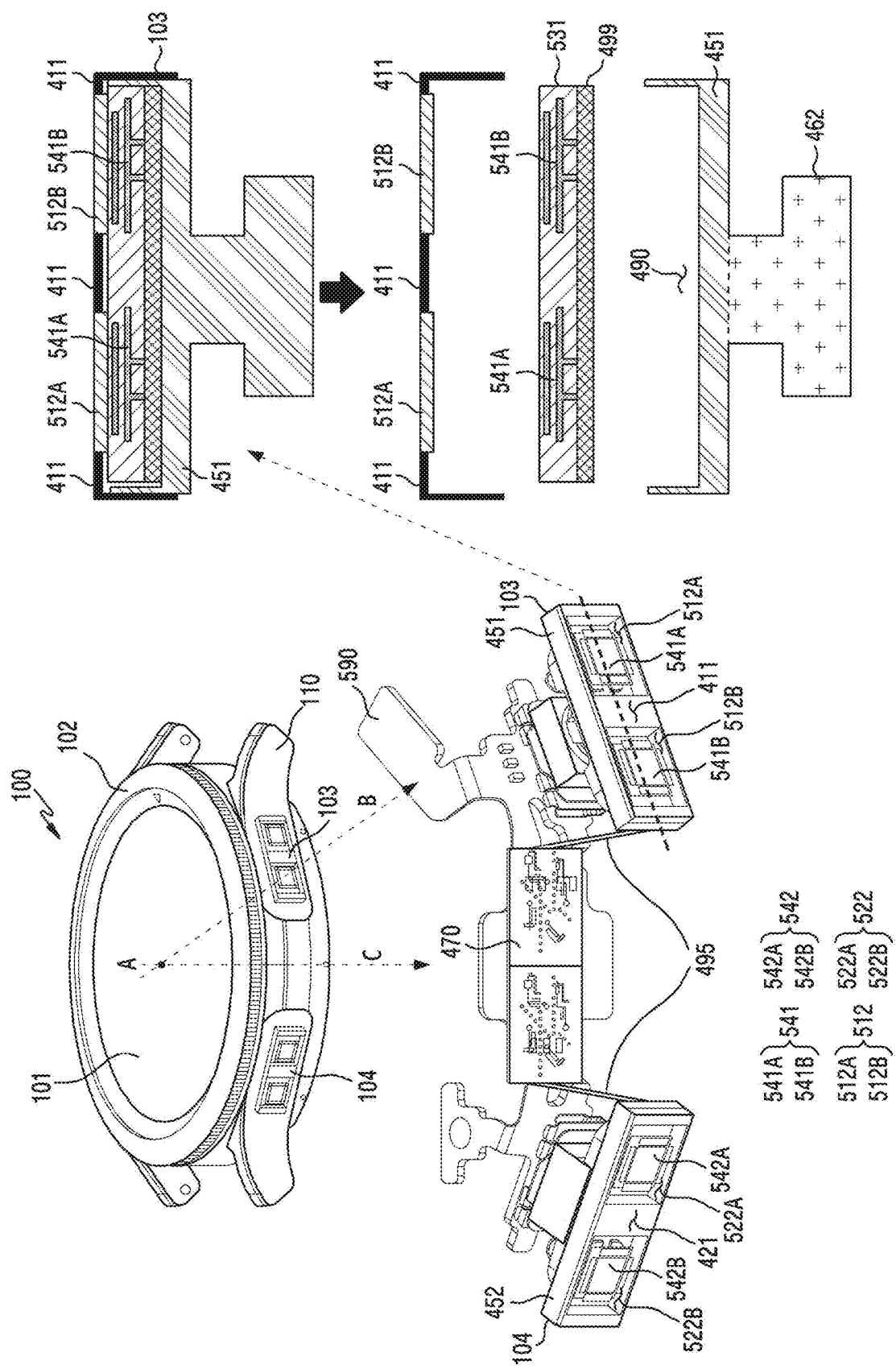
FIG. 5A illustrates a wearable device including an input member and a patch antenna having a 1×2 structure according to an embodiment of the disclosure.
Figure 5B:
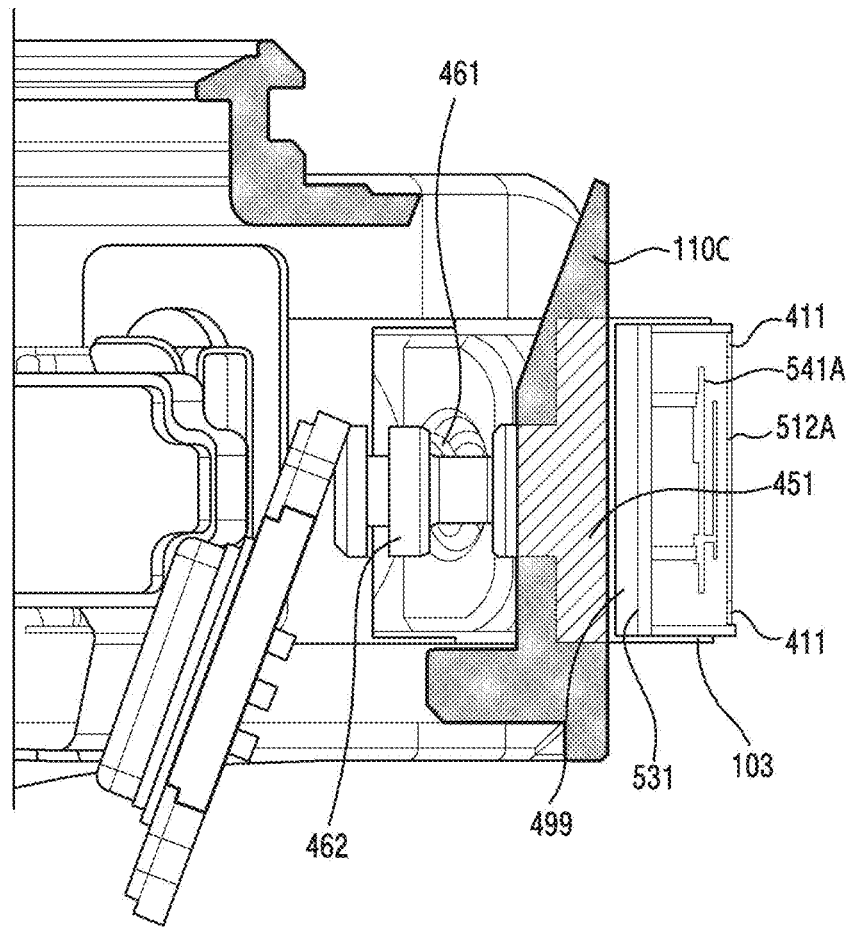
FIG. 5B is a cross-sectional view taken along axis A-B of the wearable device of FIG. 5A according to an embodiment of the disclosure.
Figure 5C:
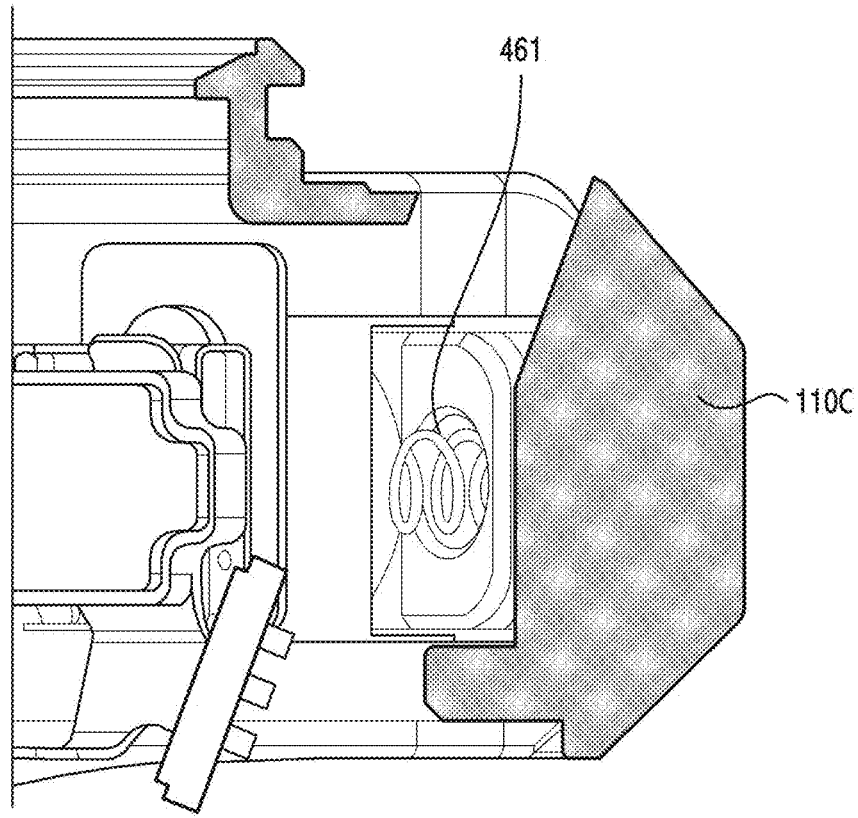
FIG. 5C is a cross-sectional view taken along axis A-C of the wearable device of FIG. 5A according to an embodiment of the disclosure.

FIG. 5A illustrates a wearable device including an input member and a patch antenna having a 1×2 structure according to an embodiment of the disclosure. FIG. 5B is a cross-sectional view taken along axis A-B of the wearable device of FIG. 5A according to an embodiment of the disclosure. FIG. 5C is a cross-sectional view taken along axis A-C of the wearable device of FIG. 5A according to an embodiment of the disclosure.

Referring to FIGS. 5A to 5C together, the wearable device 100 according to an embodiment may include an input member 103 or 104 and a patch antenna 541 or 542 disposed to face the input member 103 or 104. The same reference numerals are used for the same or substantially the same components as those described above, and overlapping descriptions will be omitted.

According to an embodiment, the wearable device 100 may include a first PCB 531 disposed on the first metal member 451. According to an embodiment, the first PCB 531 may be disposed on the first recess 490 formed on one surface of the first metal member 451.

According to an embodiment, the first PCB 531 may include a (1-1)th PCB positioned at a location corresponding to a (1-1)th non-conductive portion 512A, and a (1-2)th PCB disposed at a location corresponding to a (1-2)th non-conductive portion 512B. According to another embodiment, the first PCB 531 may be referred to as a single, integrally formed PCB.

According to an embodiment, the wearable device 100 may include a first antenna array 541 disposed on the first PCB 531. According to an embodiment, the wearable device 100 may include, on the first PCB 531, the first antenna array 541 disposed at a location corresponding to the first non-conductive portion 512. For example, the first non-conductive portion 512 may include the (1-1)th non-conductive portion 512A or the (1-2)th non-conductive portion 512B.

According to an embodiment, the wiring layer 499 included in the first PCB 531 may be configured to be connected to the wireless communication circuit 470 through the connection unit 590 so as to transmit the signal transmitted from the wireless communication circuit 470 to the first antenna array 541 (or an antenna radiator). The connection unit 590 according to an embodiment may be referred to as a connector configured to connect a printed circuit board (e.g., the printed circuit board 380 of FIG. 3) to the first PCB 531.

According to an embodiment, the first antenna array 541 may include a (1-1)th conductive patch 541A disposed at a location corresponding to the (1-1)th non-conductive portion 512A, and a (1-2)th conductive patch 541B disposed at a location corresponding to the (1-2) non-conductive portion 512B.

According to an embodiment, the wearable device 100 may include a second PCB disposed on the second metal member 452. According to an embodiment, the second PCB may be disposed on a second recess formed on one surface of the second metal member 452. According to an embodiment, the second PCB may be referred to as having a shape corresponding to that of the first PCB 531.

According to an embodiment, the wearable device 100 may include a second antenna array 542 disposed on a second PCB. According to an embodiment, the wearable device 100 may include, on the second PCB, a second antenna array 542 disposed at a location corresponding to the second non-conductive portion 522. For example, the second non-conductive portion 522 may include a (2-1)th non-conductive portion 522A or a (2-2)th non-conductive portion 522B.

According to an embodiment, the second antenna array 542 may include a (2-1)th conductive patch 542A disposed at a location corresponding to the (2-1)th non-conductive portion 522A, and a (2-2)th conductive patch 542B disposed at a location corresponding to the (2-2)th non-conductive portion 522B.

According to an embodiment, the (1-1)th conductive patch 541A, the (1-2)th conductive patch 541B, the (2-1)th conductive patch 542A, or the (2-2)th conductive patch 542B may be formed substantially the same as the first conductive patch 441 and the second conductive patch 442 of FIG. 4A.

According to an embodiment, the wireless communication circuit 470 may be electrically connected to the first antenna array 541 and/or the second antenna array 542 through the conductive connection member 495.

According to an embodiment, the wireless communication circuit 470 may transmit and/or receive a signal of the first frequency band by using the first antenna array 541 and/or the second antenna array 542 through the conductive connection member 495. For example, the wireless communication circuit 470 may transmit and/or receive an mmWave signal by feeding power to the (1-1)th conductive patch 541A and the (1-2)th conductive patch 541B through the conductive connection member 495. For another example, the wireless communication circuit 470 may transmit and/or receive an mmWave signal by feeding power to the (2-1)th conductive patch 542A and the (2-2)th conductive patch 542B through the conductive connecting member 495. For example, the mmWave signal may include a signal in a frequency band of about 28 GHz, 36 GHz, or 60 GHz.

According to an embodiment, the wireless communication circuit 470 may radiate a signal of the first frequency band in a direction toward the first non-conductive portion 512 by feeding power to the first antenna array 541. According to an embodiment, the wireless communication circuit 470 may radiate a signal of the first frequency band in a direction toward the second non-conductive portion 522 by feeding power to the second antenna array 542.

Figure 6A:
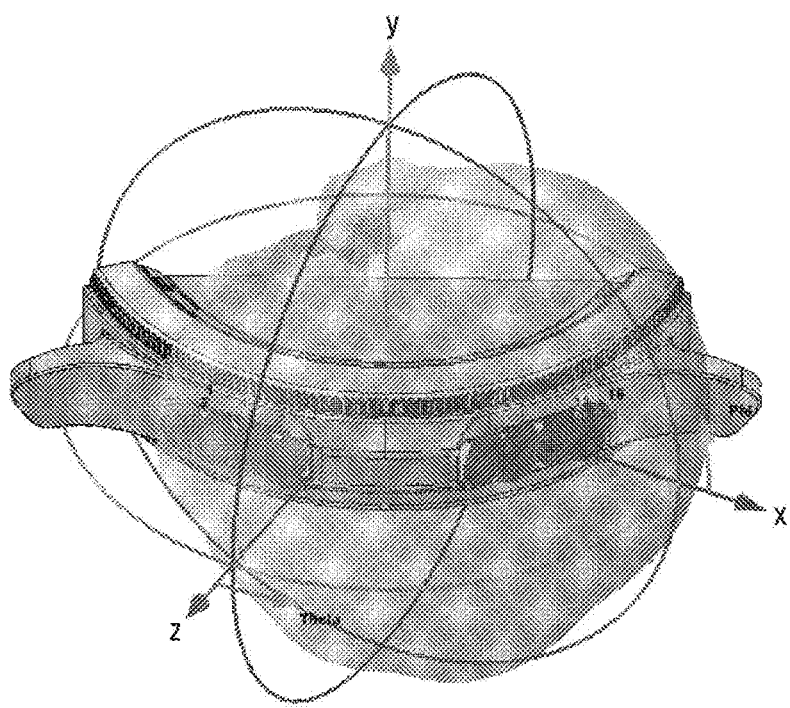
FIG. 6A illustrates a radiation pattern of a signal radiated through at least a portion of a first input member according to an embodiment of the disclosure.
Figure 6B:
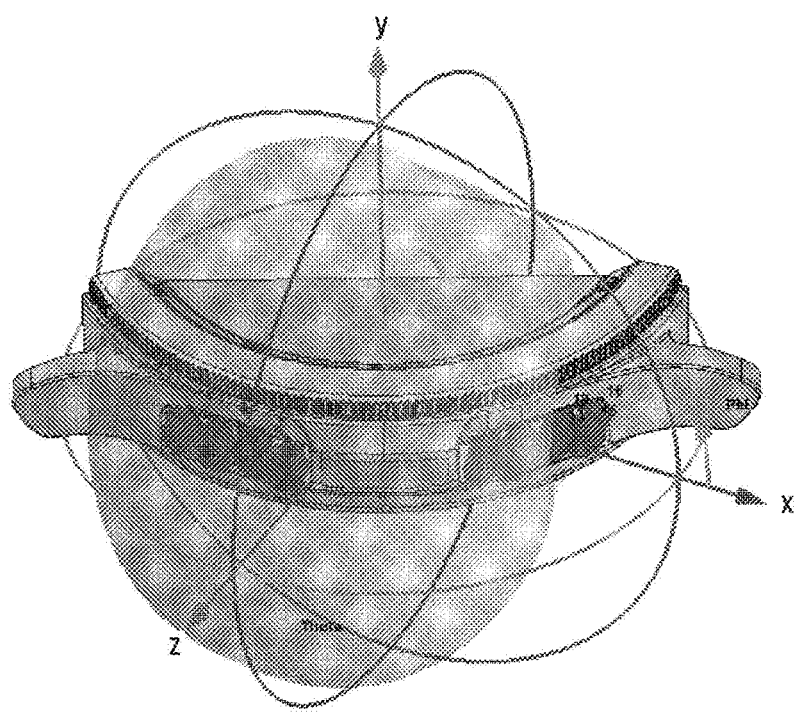
FIG. 6B illustrates a radiation pattern of a signal radiated through at least a portion of a second input member according to an embodiment of the disclosure.

FIG. 6A illustrates a radiation pattern of a signal radiated through at least a portion of a first input member according to an embodiment of the disclosure. FIG. 6B illustrates a radiation pattern of a signal radiated through at least a portion of a second input member according to an embodiment of the disclosure.

Referring to FIGS. 6A and 6B together, the wireless communication circuit (e.g., the wireless communication circuit 470 of FIG. 4A and/or FIG. 5A) may transmit a signal of a specified frequency by feeding power to at least one of a first antenna array (e.g., the first antenna array 541 of FIG. 5A) or a second antenna array (e.g., the second antenna array 542 of FIG. 5A) (or at least one of the first conductive patch 441 or the second conductive patch 442 of FIG. 4A).

Referring to FIG. 6A, the wireless communication circuit 470 according to an embodiment may transmit a signal of a first frequency band by feeding power to the first conductive patch 441 or the first antenna array 541. According to an embodiment, the wireless communication circuit 470 may radiate a signal of the first frequency band by feeding power to the first conductive patch 441 or the first antenna array 541. According to an embodiment, the wireless communication circuit 470 may form a radiation pattern as shown in FIG. 6A by feeding power to the first conductive patch 441 or the first antenna array 541.

Referring to FIG. 6B, the wireless communication circuit 470 according to an embodiment may transmit a signal of the first frequency band by feeding power to the second conductive patch 442 or the second antenna array 542. According to an embodiment, the wireless communication circuit 470 may radiate a signal of the first frequency band by feeding power to the second conductive patch 442 or the second antenna array 542. According to an embodiment, the wireless communication circuit 470 may form a radiation pattern as shown in FIG. 6B by feeding power to the second conductive patch 442 or the second antenna array 542.

Figure 7A:
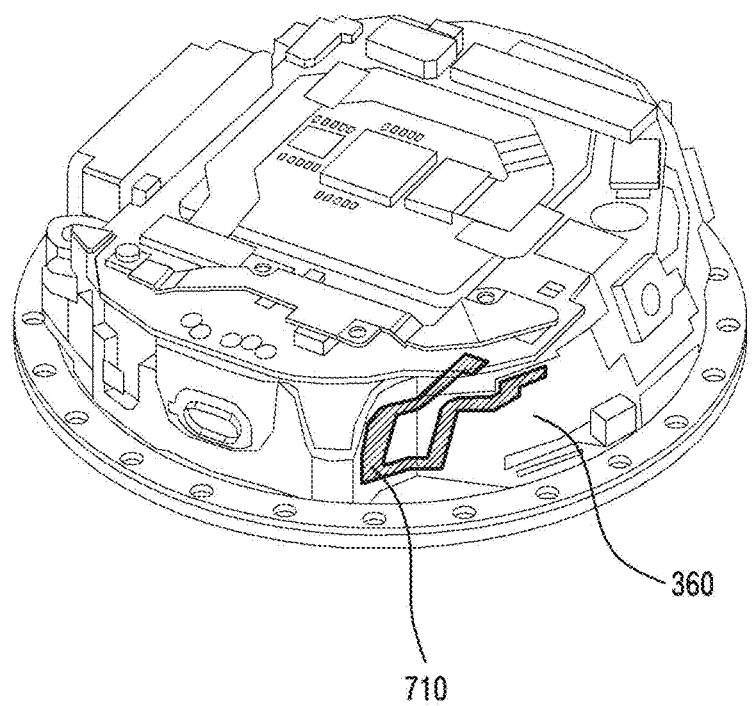
FIG. 7A illustrates a conductive pattern disposed on a support member of a wearable device according to an embodiment of the disclosure.
Figure 7B:
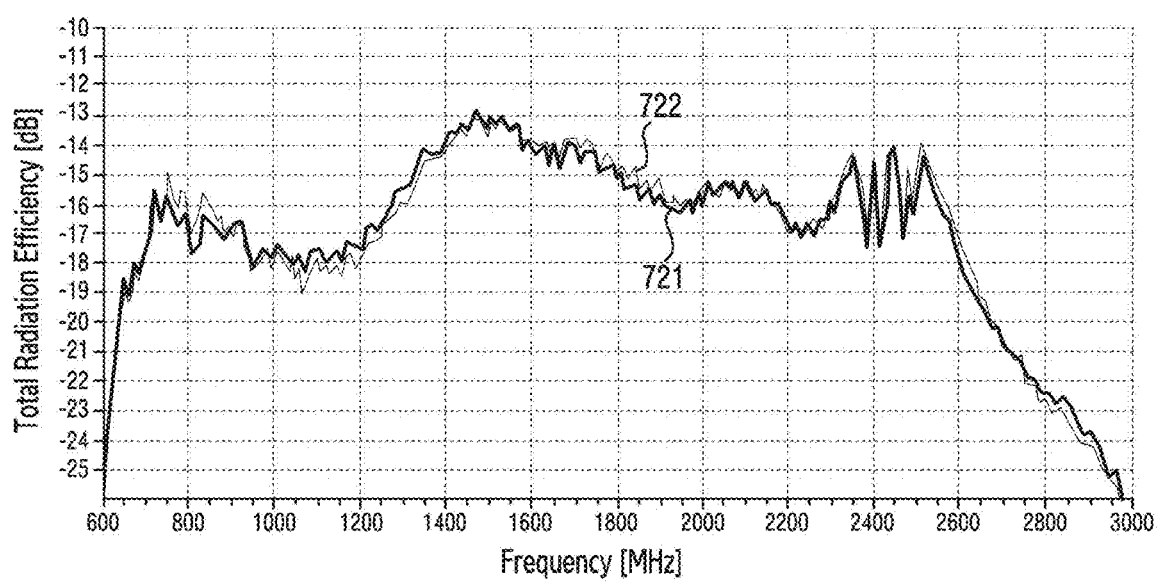
FIG. 7B illustrates radiation efficiency of a signal radiated through a housing and a conductive pattern according to an embodiment of the disclosure.

FIG. 7A illustrates a conductive pattern disposed on a support member of a wearable device according to an embodiment of the disclosure. FIG. 7B illustrates radiation efficiency of a signal radiated through a housing and a conductive pattern according to an embodiment of the disclosure.

Referring to FIGS. 7A and 7B together, the wearable device (e.g., the wearable device 100 of FIG. 4A and/or FIG. 5A) according to an embodiment may include a conductive pattern 710 formed on a support member 360 (e.g., the support member 360 of FIG. 3). According to an embodiment, the wearable device 100 may include the support member 360 formed inside a housing (e.g., the housing 110 of FIG. 1, FIG. 4A, and/or FIG. 5A), and the conductive pattern 710 formed on one surface of the support member 360. According to an embodiment, a wireless communication circuit (not shown) disposed on a printed circuit board (e.g., the printed circuit board 380 of FIG. 3) may be electrically connected to at least a portion of the housing 110 and/or the conductive pattern 710.

The wireless communication circuit (not shown) according to an embodiment may be referred to as a separate configuration that is distinct from the wireless communication circuit 470 of FIGS. 4A and 5A. For example, the wireless communication circuit (not shown) may support legacy communication such as LTE or BT.

According to an embodiment, at least a portion of a lateral bezel structure (e.g., the lateral bezel structure 310 of FIG. 3) may be formed of a conductive material. According to an embodiment, at least a portion of the lateral surface of the housing 110 (e.g., the lateral surface 110C of FIGS. 2, 4B, 4C, 5B, and/or FIG. 5C) may be formed of a conductive material (e.g., metal).

According to an embodiment, the wireless communication circuit (not shown) may be electrically connected to at least a portion of the lateral bezel structure 310. According to an embodiment, the wireless communication circuit (not shown) may be electrically connected to a portion of the lateral bezel structure 310 formed of a conductive material.

According to an embodiment, the wireless communication circuit (not shown) may transmit and/or receive a signal of a third frequency band by feeding power to a portion of the lateral bezel structure 310 formed of the conductive material. For example, the wireless communication circuit (not shown) may transmit and/or receive a signal of a long-term evolution (LTE) band by feeding power to a portion of the lateral bezel structure 310 formed of a conductive material. For example, the wireless communication circuit (not shown) may transmit and/or receive a signal of about 1500 MHz band by feeding power to a portion of the lateral bezel structure 310 formed of a conductive material. For another example, the wireless communication circuit (not shown) may transmit and/or receive a signal in a global positioning system (GPS) frequency band (e.g., about 1 GHz to about 2 GHz) by feeding power to a portion of the lateral bezel structure 310 formed of a conductive material.

According to an embodiment, the wireless communication circuit (not shown) may transmit and/or receive a signal of a fourth frequency band by feeding power to the conductive pattern 710. For example, the wireless communication circuit (not shown) may transmit and/or receive a signal of a Bluetooth or wireless fidelity (Wi-Fi) band by feeding power to the conductive pattern 710. For example, the wireless communication circuit (not shown) may transmit a Bluetooth signal of about 2.4 GHz band by feeding power to the conductive pattern 710.

Referring to FIG. 7B, according to an embodiment, the wearable device 100 may have a first radiation efficiency 721 when power is supplied to at least a portion of the housing 110 and the conductive pattern 710 in a state in which the wearable device 100 does not include a first antenna array (e.g., the first antenna array 541 of FIG. 5A) and a second antenna array (e.g., the second antenna array 542 of FIG. 5A) (alternately, the first conductive patch 441 and the second conductive patch 442 of FIG. 4A).

According to another embodiment, the wearable device 100 may have a second radiation efficiency 722 that is substantially the same as or similar to the first radiation efficiency 721 when power is supplied to at least a portion of the housing 110 and the conductive pattern 710 in a state in which the wearable device 100 does not include the first antenna array 541 and the second antenna array 542 (alternately, the first conductive patch 441 and the second conductive patch 442 of FIG. 4A).

According to an embodiment, when the wearable device 100 includes the first antenna array 541 and the second antenna array 542 (alternately, the first conductive patch 441 and the second conductive patch 442), the radiation efficiency of a signal radiated through at least a portion of the housing 110 and the conductive pattern 710 may be maintained substantially the same as or similar to the case in which the wearable device 100 does not include the first antenna array 541 and the second antenna array 542 (alternately, the first conductive patch 441 and the second conductive patch 442).

Figure 8A:
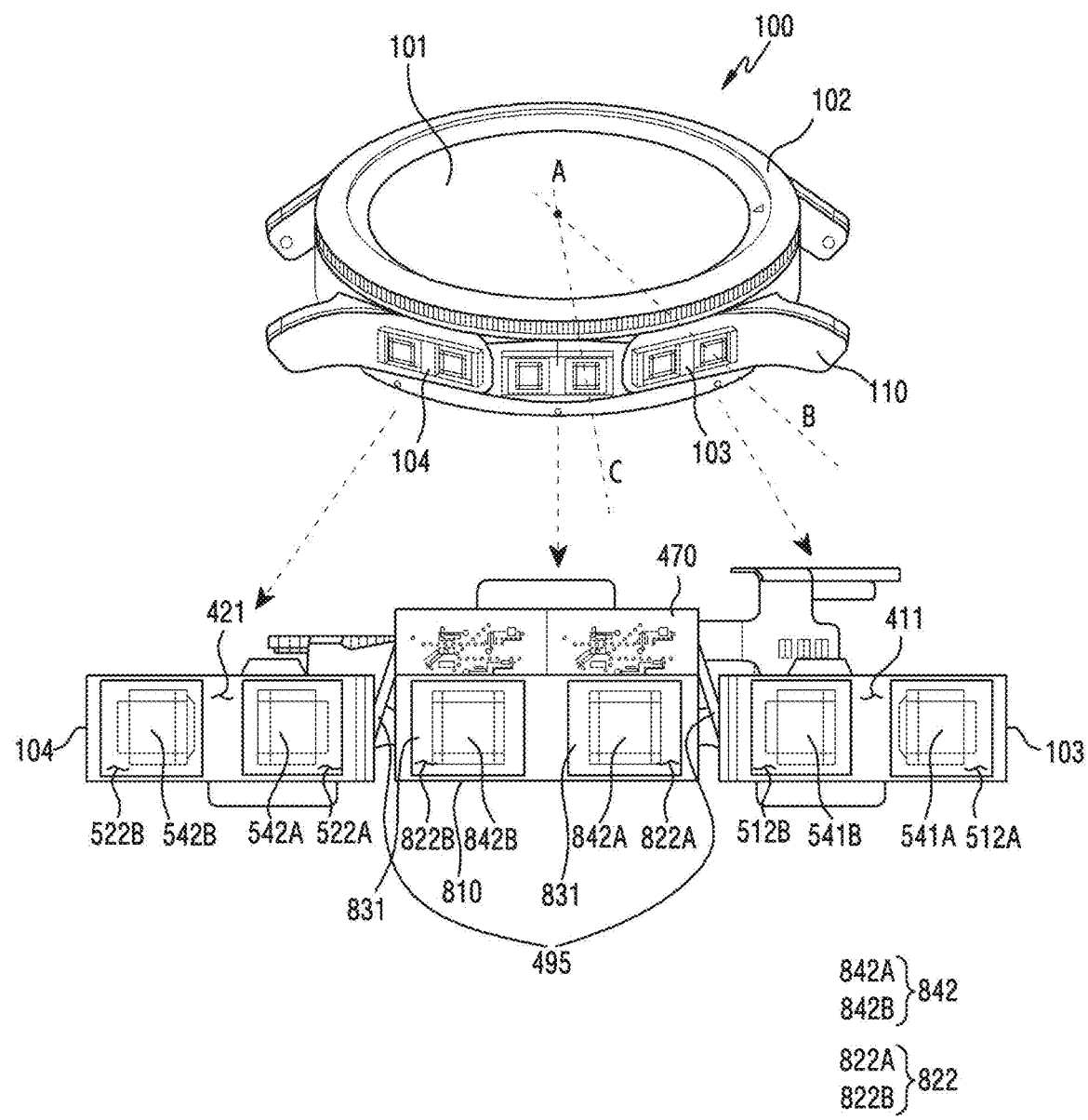
FIG. 8A illustrates a wearable device further including an input member and a third antenna array having a 1×2 structure according to an embodiment of the disclosure.
Figure 8B:
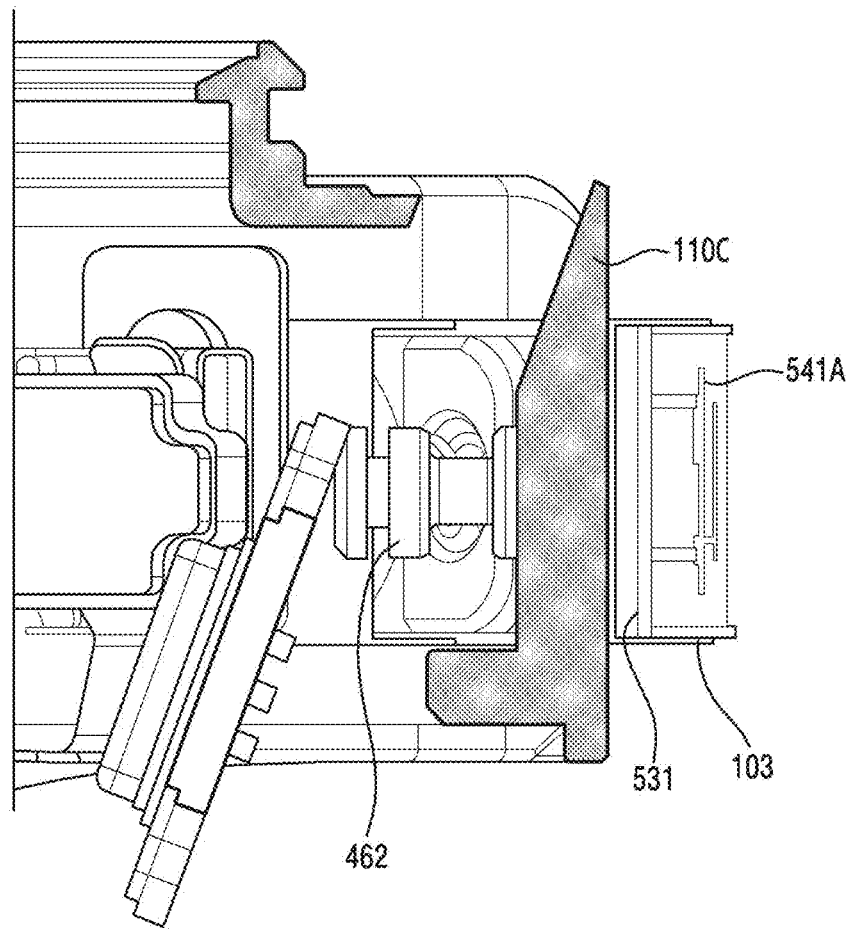
FIG. 8B is a cross-sectional view taken along axis A-B of the wearable device of FIG. 8A according to an embodiment of the disclosure.
Figure 8C:
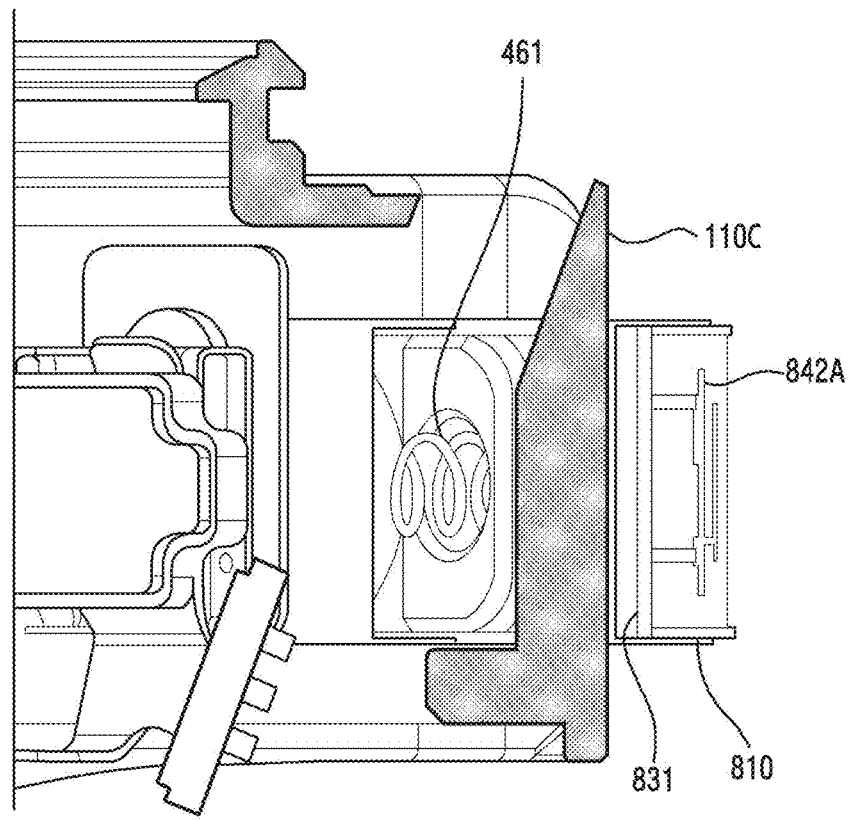
FIG. 8C is a cross-sectional view taken along axis A-C of the wearable device of FIG. 8A according to an embodiment of the disclosure.

FIG. 8A illustrates a wearable device further including an input member and a third antenna array having a 1×2 structure according to an embodiment of the disclosure. FIG. 8B is a cross-sectional view taken along axis A-B of the wearable device of FIG. 8A according to an embodiment of the disclosure. FIG. 8C is a cross-sectional view taken along axis A-C of the wearable device of FIG. 8A according to an embodiment of the disclosure.

Referring to FIGS. 8A to 8C, the wearable device 100 according to an embodiment may further include a third input member 810 formed on the lateral surface 110C of the housing 110. The wearable device 100 according to an embodiment may further include a third PCB 831 disposed inside the housing 110 and a third antenna array 842 disposed on the third PCB 831. The same or substantially the same components as those described above have the same reference numerals, and overlapping descriptions will be omitted.

According to an embodiment, the housing 110 of the wearable device 100 may include a third non-conductive portion 822 formed on one surface of the third input member 810. According to an embodiment, the third non-conductive portion 822 of the third input member 810 may include a (3-1)th non-conductive portion 822A and a (3-2)th non-conductive portion 822B which are formed to be spaced apart from each other. According to another embodiment, the (3-1)th non-conductive portion 822A and the (3-2)th non-conductive portion 822B may be integrally formed with each other to form a single non-conductive region.

According to an embodiment, the wearable device 100 may include a third PCB 831 disposed inside the housing 110 to face the lateral surface 110C. According to an embodiment, the wearable device 100 may include the third PCB 831 disposed inside the housing 110 to face the third non-conductive portion 822 of the third input member 810 formed on the lateral surface 110C. According to an embodiment, the third PCB 831 may be disposed between the first PCB and the second PCB described above with reference to FIG. 4A and/or FIG. 5A inside the housing 110. According to an embodiment, the third PCB 831 may be disposed to overlap at least a portion of the wireless communication circuit 470 when viewed from the center of the housing 110. According to an embodiment, the third PCB 831 may be disposed to overlap at least a portion of the third non-conductive portion 822 when viewed from the center of the housing 110.

According to an embodiment, the wearable device 100 may include the third antenna array 842 including at least one conductive patch 842A or 842B disposed on the third PCB 831. According to an embodiment, the wearable device 100 may include the third antenna array 842 disposed on one surface of the third PCB 831 toward the third non-conductive portion 822. According to an embodiment, the wearable device 100 may include, on the third PCB 831, the third antenna array 842 including at least one conductive patch 842A or 842B disposed in a region corresponding to the third non-conductive part 822.

According to an embodiment, the third antenna array 842 may include a (3-1)th conductive patch 842A disposed in a region corresponding to the (3-1)th non-conductive portion 822A, and a (3-2)th conductive patch 842B disposed in a region corresponding to the (3-2)th non-conductive portion 822B. According to another embodiment (not shown), the (3-1)th conductive patch 842A and the (3-2)th conductive patch 842B may be integrally formed with each other to form a single patch.

According to an embodiment, the wireless communication circuit 470 may transmit and/or receive a signal (e.g., an mmWave signal) of the first frequency band by feeding power to at least a portion of the first antenna array 541, the second antenna array 542, and the third antenna array 842. For example, the wireless communication circuit 470 may transmit a signal of about 28 GHz band by feeding power to the third antenna array 842. For example, the wireless communication circuit 470 may radiate a signal of the first frequency band toward the third non-conductive portion 822 by feeding power to the third antenna array 842.

Figure 9A:
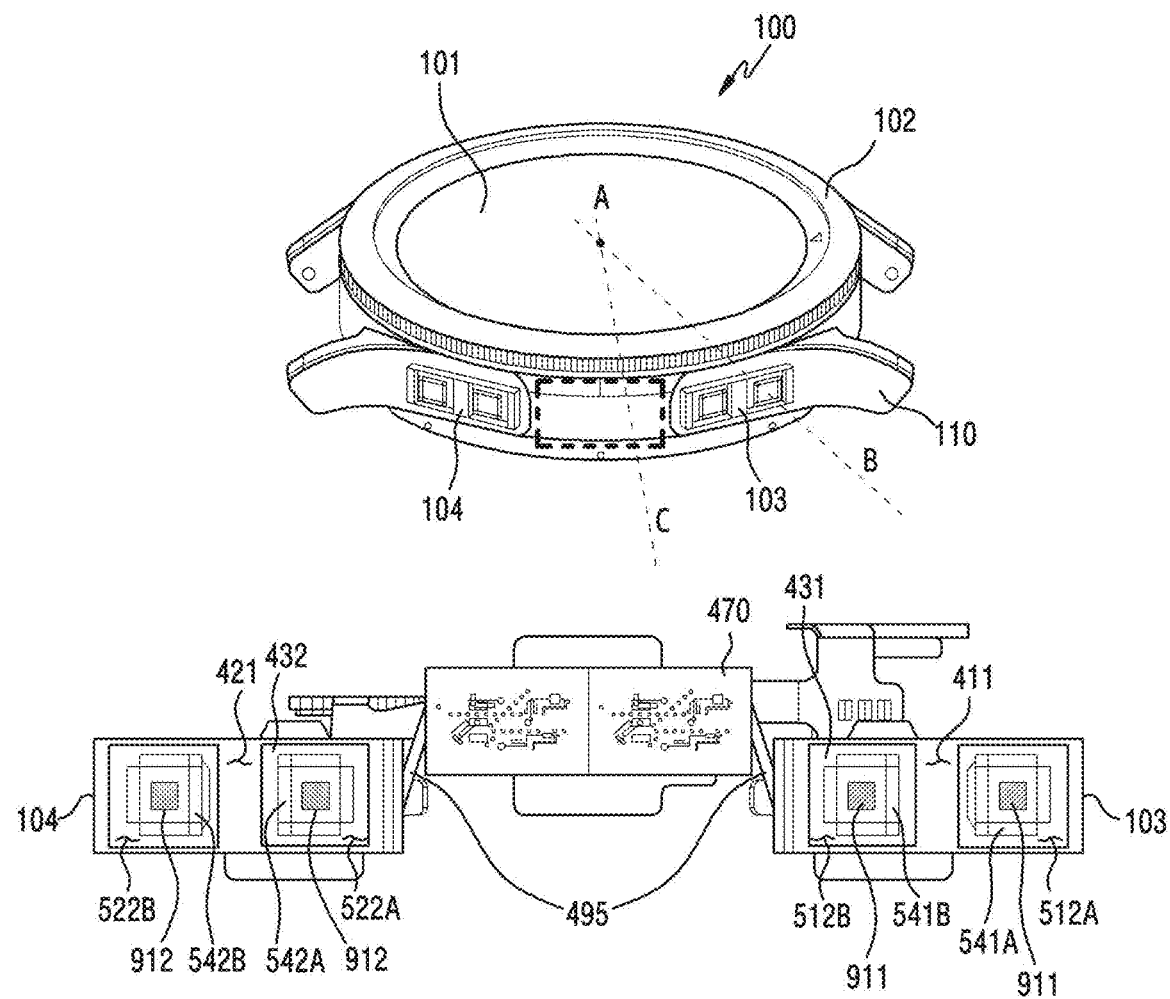
FIG. 9A illustrates the wearable device of FIG. 5A further including a fourth antenna array according to an embodiment of the disclosure.
Figure 9B:
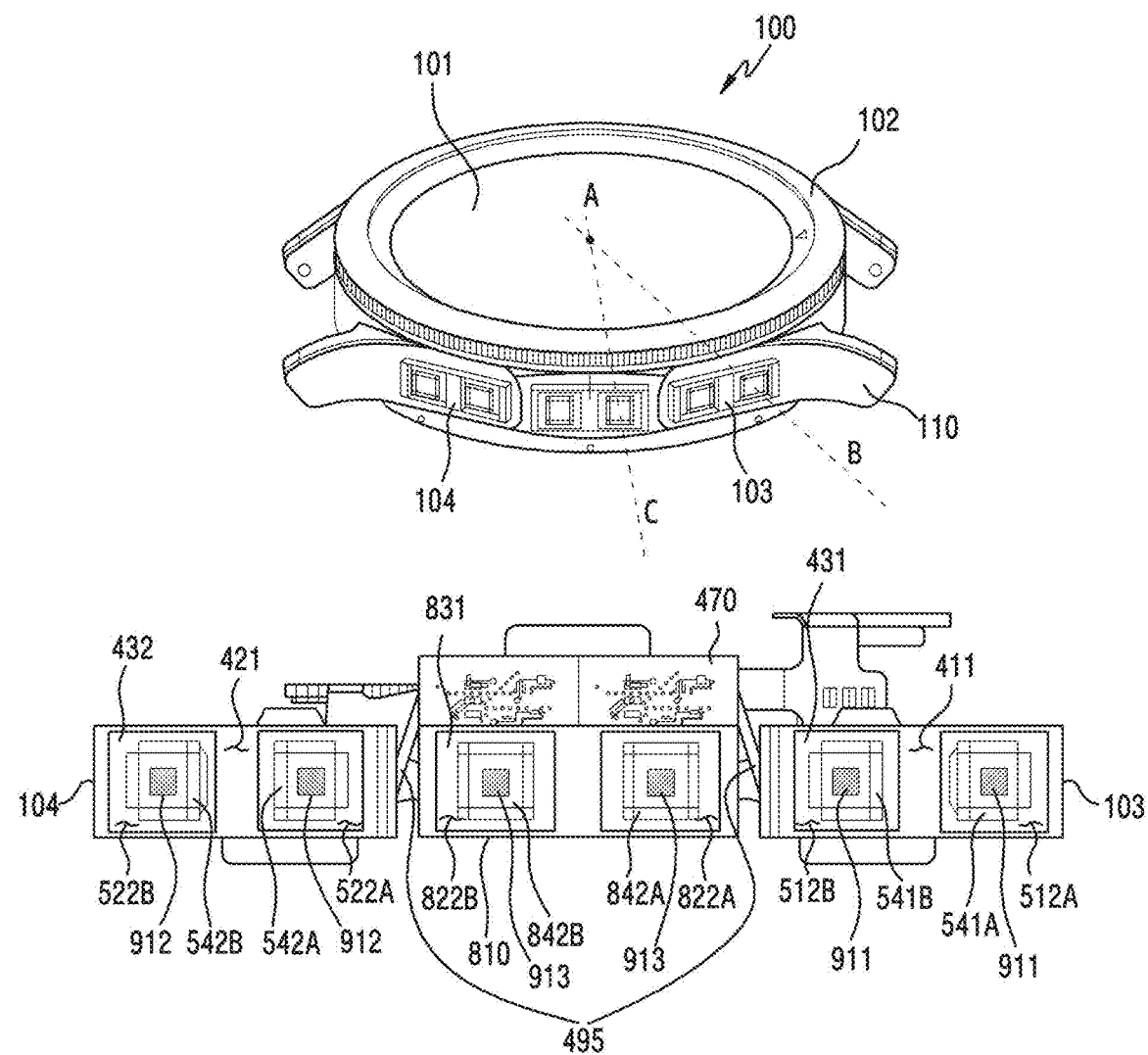
FIG. 9B illustrates the wearable device of FIG. 8A further including a fourth antenna array according to an embodiment of the disclosure.

FIG. 9A illustrates the wearable device of FIG. 5A further including a fourth antenna array according to an embodiment of the disclosure. FIG. 9B illustrates the wearable device of FIG. 8A further including a fourth antenna array according to an embodiment of the disclosure.

Referring to FIG. 9A, at least one of the PCBs 431 and 432 according to an embodiment may further include a dielectric layer disposed on the antenna array 541 or 542, and a (4-1)th antenna array 911 and a (4-2)th antenna array 912 which are disposed on the dielectric layer. In this case, the (4-2)th antenna array 912 may be formed to be substantially the same as the (4-1)th antenna array 911.

Referring to FIG. 9B, the third PCB 831 according to an embodiment may further include a dielectric layer disposed on the third antenna array 842, and a (4-3)th antenna array 913 disposed on the dielectric layer. In this case, the (4-3)th antenna array 913 may be formed to be substantially the same as the (4-1)th antenna array 911.

According to an embodiment, the first PCB 431 may include a dielectric layer disposed on the first antenna array 541, and the (4-1)th antenna array 911 disposed on the dielectric layer. According to an embodiment, the second PCB 432 may include a dielectric layer disposed on the second antenna array 542, and the (4-2)th antenna array 912 disposed on the dielectric layer. According to an embodiment, the third PCB 831 may include a dielectric layer disposed on the third antenna array 842, and the (4-3)th antenna array 913 disposed on the dielectric layer.

According to an embodiment, the fourth antenna array 911, 912, or 913 may have a smaller area than the first antenna array 541, the second antenna array 542, and the third antenna array 842. According to an embodiment, each of the conductive patches included in the fourth antenna arrays 911, 912, and 913 may have a smaller area than the conductive patch of each of the first antenna array 541, the second antenna array 542, and the third antenna array 842. For example, the (4-1)th antenna array 911 may have a smaller area than the first antenna array 541. In addition, the (4-2)th antenna array 912 may have a smaller area than the second antenna array 542.

According to an embodiment, the wireless communication circuit 470 may transmit a signal (e.g., a Wi-Fi signal) of the second frequency band by feeding power to the fourth antenna array 911, 912, or 913. For example, the wireless communication circuit 470 may transmit and/or receive a signal of about 60 GHz band by feeding power to the fourth antenna array 911, 912, or 913. According to an embodiment, the wireless communication circuit 470 may transmit a signal of the first frequency band (e.g., about 28 GHz) by feeding power to the first antenna array 541 or the third antenna array 842, and may transmit a signal of the second frequency band (e.g., about 60 GHz) by feeding power to the fourth antenna array 911, 912, or 913.

According to an embodiment, the wireless communication circuit 470 may radiate a signal of the second frequency band toward the first non-conductive portion 512 by feeding power to the (4-1)th antenna array 911. According to an embodiment, the wireless communication circuit 470 may radiate a signal of the second frequency band toward the second non-conductive portion 522 by feeding power to the (4-2)th antenna array 912. According to an embodiment, the wireless communication circuit 470 may radiate a signal of the second frequency band toward the third non-conductive portion 822 by feeding power to the (4-3)th antenna array 913.

Figure 10:
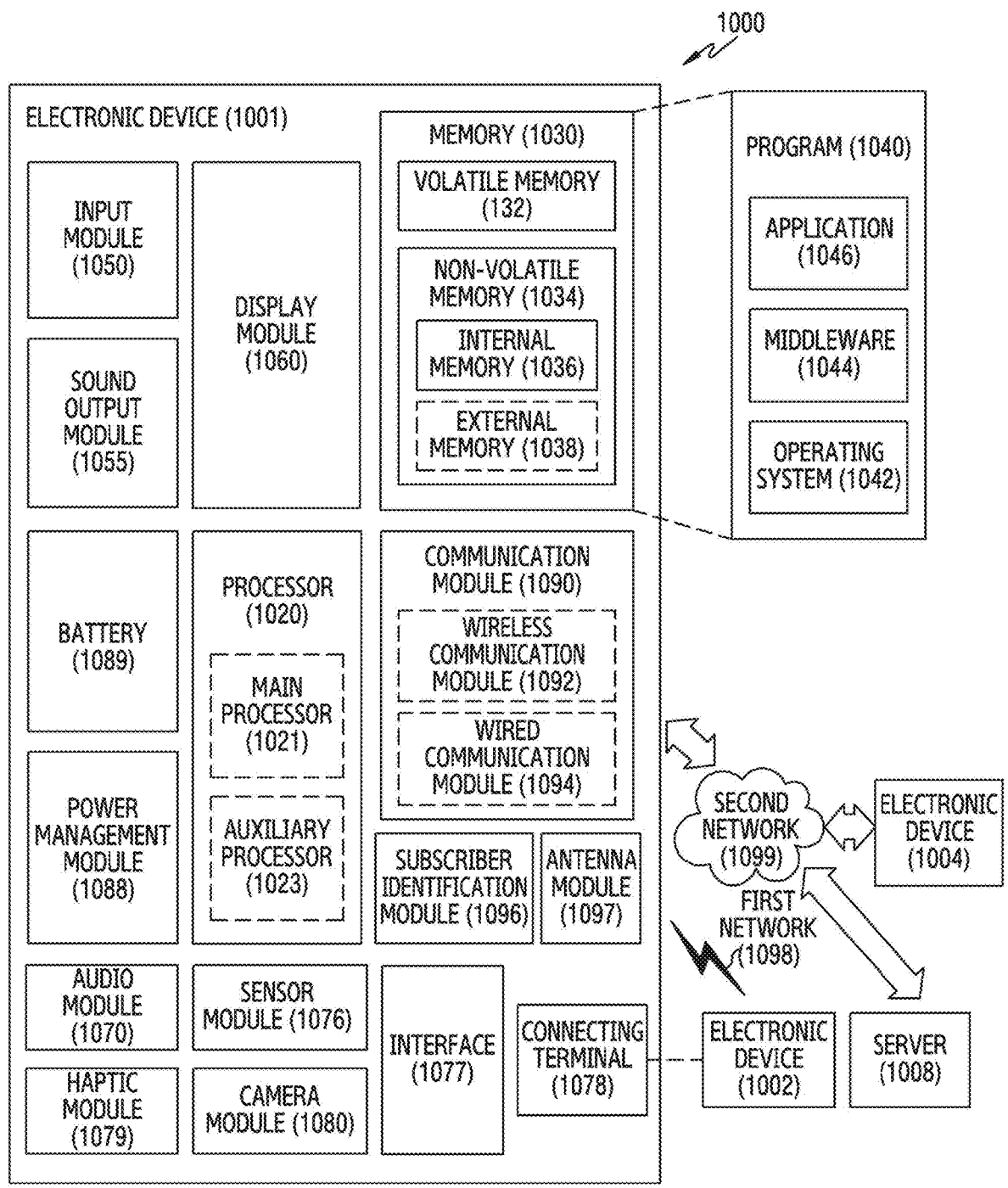
FIG. 10 is a block diagram of an electronic device in a network environment according to an embodiment of the disclosure.

FIG. 10 is a block diagram of an electronic device in a network environment according to an embodiment of the disclosure.

Referring to FIG. 10, the electronic device 1001 in the network environment 1000 may communicate with an electronic device 1002 via a first network 1098 (e.g., a short-range wireless communication network), or at least one of an electronic device 1004 or a server 1008 via a second network 1099 (e.g., a long-range wireless communication network). According to an embodiment, the electronic device 1001 may communicate with the electronic device 1004 via the server 1008. According to an embodiment, the electronic device 1001 may include a processor 1020, memory 1030, an input module 1050, a sound output module 1055, a display module 1060, an audio module 1070, a sensor module 1076, an interface 1077, a connecting terminal 1078, a haptic module 1079, a camera module 1080, a power management module 1088, a battery 1089, a communication module 1090, a subscriber identification module (SIM) 1096, or an antenna module 1097. In some embodiments, at least one of the components (e.g., the connecting terminal 1078) may be omitted from the electronic device 1001, or one or more other components may be added in the electronic device 1001. In some embodiments, some of the components (e.g., the sensor module 1076, the camera module 1080, or the antenna module 1097) may be implemented as a single component (e.g., the display module 1060).

The processor 1020 may execute, for example, software (e.g., a program 1040) to control at least one other component (e.g., a hardware or software component) of the electronic device 1001 coupled with the processor 1020, and may perform various data processing or computation. According to one embodiment, as at least part of the data processing or computation, the processor 1020 may store a command or data received from another component (e.g., the sensor module 1076 or the communication module 1090) in volatile memory 1032, process the command or the data stored in the volatile memory 1032, and store resulting data in non-volatile memory 1034. According to an embodiment, the processor 1020 may include a main processor 1021 (e.g., a central processing unit (CPU) or an application processor (AP)), or an auxiliary processor 1023 (e.g., a graphics processing unit (GPU), a neural processing unit (NPU), an image signal processor (ISP), a sensor hub processor, or a communication processor (CP)) that is operable independently from, or in conjunction with, the main processor 1021. For example, when the electronic device 1001 includes the main processor 1021 and the auxiliary processor 1023, the auxiliary processor 1023 may be adapted to consume less power than the main processor 1021, or to be specific to a specified function. The auxiliary processor 1023 may be implemented as separate from, or as part of the main processor 1021.

The auxiliary processor 1023 may control at least some of functions or states related to at least one component (e.g., the display module 1060, the sensor module 1076, or the communication module 1090) among the components of the electronic device 1001, instead of the main processor 1021 while the main processor 1021 is in an inactive (e.g., sleep) state, or together with the main processor 1021 while the main processor 1021 is in an active state (e.g., executing an application). According to an embodiment, the auxiliary processor 1023 (e.g., an image signal processor or a communication processor) may be implemented as part of another component (e.g., the camera module 1080 or the communication module 1090) functionally related to the auxiliary processor 1023. According to an embodiment, the auxiliary processor 1023 (e.g., the neural processing unit) may include a hardware structure specified for artificial intelligence model processing. An artificial intelligence model may be generated by machine learning. Such learning may be performed, e.g., by the electronic device 1001 where the artificial intelligence is performed or via a separate server (e.g., the server 1008). Learning algorithms may include, but are not limited to, e.g., supervised learning, unsupervised learning, semi-supervised learning, or reinforcement learning. The artificial intelligence model may include a plurality of artificial neural network layers. The artificial neural network may be a deep neural network (DNN), a convolutional neural network (CNN), a recurrent neural network (RNN), a restricted boltzmann machine (RBM), a deep belief network (DBN), a bidirectional recurrent deep neural network (BRDNN), deep Q-network or a combination of two or more thereof but is not limited thereto. The artificial intelligence model may, additionally or alternatively, include a software structure other than the hardware structure.

The memory 1030 may store various data used by at least one component (e.g., the processor 1020 or the sensor module 1076) of the electronic device 1001. The various data may include, for example, software (e.g., the program 1040) and input data or output data for a command related thereto. The memory 1030 may include the volatile memory 1032 or the non-volatile memory 1034.

The program 1040 may be stored in the memory 1030 as software, and may include, for example, an operating system (OS) 1042, middleware 1044, or an application 1046.

The input module 1050 may receive a command or data to be used by another component (e.g., the processor 1020) of the electronic device 1001, from the outside (e.g., a user) of the electronic device 1001. The input module 1050 may include, for example, a microphone, a mouse, a keyboard, a key (e.g., a button), or a digital pen (e.g., a stylus pen).

The sound output module 1055 may output sound signals to the outside of the electronic device 1001. The sound output module 1055 may include, for example, a speaker or a receiver. The speaker may be used for general purposes, such as playing multimedia or playing record. The receiver may be used for receiving incoming calls. According to an embodiment, the receiver may be implemented as separate from, or as part of the speaker.

The display module 1060 may visually provide information to the outside (e.g., a user) of the electronic device 1001. The display module 1060 may include, for example, a display, a hologram device, or a projector and control circuitry to control a corresponding one of the displays, hologram device, and projector. According to an embodiment, the display module 1060 may include a touch sensor adapted to detect a touch, or a pressure sensor adapted to measure the intensity of force incurred by the touch.

The audio module 1070 may convert a sound into an electrical signal and vice versa. According to an embodiment, the audio module 1070 may obtain the sound via the input module 1050, or output the sound via the sound output module 1055 or a headphone of an external electronic device (e.g., an electronic device 1002) directly (e.g., wiredly) or wirelessly coupled with the electronic device 1001.

The sensor module 1076 may detect an operational state (e.g., power or temperature) of the electronic device 1001 or an environmental state (e.g., a state of a user) external to the electronic device 1001, and then generate an electrical signal or data value corresponding to the detected state. According to an embodiment, the sensor module 1076 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 1077 may support one or more specified protocols to be used for the electronic device 1001 to be coupled with the external electronic device (e.g., the electronic device 1002) directly (e.g., wiredly) or wirelessly. According to an embodiment, the interface 1077 may include, for example, a high definition multimedia interface (HDMI), a universal serial bus (USB) interface, a secure digital (SD) card interface, or an audio interface.

A connecting terminal 1078 may include a connector via which the electronic device 1001 may be physically connected with the external electronic device (e.g., the electronic device 1002). According to an embodiment, the connecting terminal 1078 may include, for example, an HDMI connector, a USB connector, an SD card connector, or an audio connector (e.g., a headphone connector).

The haptic module 1079 may convert an electrical signal into a mechanical stimulus (e.g., a vibration or a movement) or electrical stimulus which may be recognized by a user via his tactile sensation or kinesthetic sensation. According to an embodiment, the haptic module 1079 may include, for example, a motor, a piezoelectric element, or an electric stimulator.

The camera module 1080 may capture a still image or moving images. According to an embodiment, the camera module 1080 may include one or more lenses, image sensors, image signal processors, or flashes.

The power management module 1088 may manage power supplied to the electronic device 1001. According to one embodiment, the power management module 1088 may be implemented as at least part of, for example, a power management integrated circuit (PMIC).

The battery 1089 may supply power to at least one component of the electronic device 1001. According to an embodiment, the battery 1089 may include, for example, a primary cell which is not rechargeable, a secondary cell which is rechargeable, or a fuel cell.

The communication module 1090 may support establishing a direct (e.g., wired) communication channel or a wireless communication channel between the electronic device 1001 and the external electronic device (e.g., the electronic device 1002, the electronic device 1004, or the server 1008) and performing communication via the established communication channel. The communication module 1090 may include one or more communication processors that are operable independently from the processor 1020 (e.g., the application processor (AP)) and supports a direct (e.g., wired) communication or a wireless communication. According to an embodiment, the communication module 1090 may include a wireless communication module 1092 (e.g., a cellular communication module, a short-range wireless communication module, or a global navigation satellite system (GNSS) communication module) or a wired communication module 1094 (e.g., a local area network (LAN) communication module or a power line communication (PLC) module). A corresponding one of these communication modules may communicate with the external electronic device via the first network 1098 (e.g., a short-range communication network, such as Bluetooth™, Wi-Fi direct, or infrared data association (IrDA)) or the second network 1099 (e.g., a long-range communication network, such as a legacy cellular network, a 5$^{th}$ generation (5G) network, a next-generation communication network, the Internet, or a computer network (e.g., LAN or wide area network (WAN))). These various types of communication modules may be implemented as a single component (e.g., a single chip), or may be implemented as multi components (e.g., multi chips) separate from each other. The wireless communication module 1092 may identify and authenticate the electronic device 1001 in a communication network, such as the first network 1098 or the second network 1099, using subscriber information (e.g., international mobile subscriber identity (IMSI)) stored in the subscriber identification module 1096.

The wireless communication module 1092 may support a 5G network, after a 4G network, and next-generation communication technology, e.g., new radio (NR) access technology. The NR access technology may support enhanced mobile broadband (eMBB), massive machine type communications (mMTC), or ultra-reliable and low-latency communications (URLLC). The wireless communication module 1092 may support a high-frequency band (e.g., the mmWave band) to achieve, e.g., a high data transmission rate. The wireless communication module 1092 may support various technologies for securing performance on a high-frequency band, such as, e.g., beamforming, massive multiple-input and multiple-output (massive MIMO), full dimensional MIMO (FD-MIMO), array antenna, analog beam-forming, or large-scale antenna. The wireless communication module 1092 may support various requirements specified in the electronic device 1001, an external electronic device (e.g., the electronic device 1004), or a network system (e.g., the second network 1099). According to an embodiment, the wireless communication module 1092 may support a peak data rate (e.g., 20 Gbps or more) for implementing eMBB, loss coverage (e.g., 164 dB or less) for implementing mMTC, or U-plane latency (e.g., 0.5 ms or less for each of downlink (DL) and uplink (UL), or a round trip of 1 ms or less) for implementing URLLC.

The antenna module 1097 may transmit or receive a signal or power to or from the outside (e.g., the external electronic device) of the electronic device 1001. According to an embodiment, the antenna module 1097 may include an antenna including a radiating element composed of a conductive material or a conductive pattern formed in or on a substrate (e.g., a printed circuit board (PCB)). According to an embodiment, the antenna module 1097 may include a plurality of antennas (e.g., array antennas). In such a case, at least one antenna appropriate for a communication scheme used in the communication network, such as the first network 1098 or the second network 1099, may be selected, for example, by the communication module 1090 (e.g., the wireless communication module 1092) from the plurality of antennas. The signal or the power may then be transmitted or received between the communication module 1090 and the external electronic device via the selected at least one antenna. According to an embodiment, another component (e.g., a radio frequency integrated circuit (RFIC)) other than the radiating element may be additionally formed as part of the antenna module 1097.

According to various embodiments, the antenna module 1097 may form a mmWave antenna module. According to an embodiment, the mmWave antenna module may include a printed circuit board, a RFIC disposed on a first surface (e.g., the bottom surface) of the printed circuit board, or adjacent to the first surface and capable of supporting a designated high-frequency band (e.g., the mmWave band), and a plurality of antennas (e.g., array antennas) disposed on a second surface (e.g., the top or a side surface) of the printed circuit board, or adjacent to the second surface and capable of transmitting or receiving signals of the designated high-frequency band.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, commands or data may be transmitted or received between the electronic device 1001 and the external electronic device 1004 via the server 1008 coupled with the second network 1099. Each of the electronic devices 1002 or 1004 may be a device of a same type as, or a different type, from the electronic device 1001. According to an embodiment, all or some of operations to be executed at the electronic device 1001 may be executed at one or more of the external electronic devices 1002, 1004, or 1008. For example, if the electronic device 1001 should perform a function or a service automatically, or in response to a request from a user or another device, the electronic device 1001, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 1001. The electronic device 1001 may provide the outcome, with or without further processing of the outcome, as at least part of a reply to the request. To that end, a cloud computing, distributed computing, mobile edge computing (MEC), or client-server computing technology may be used, for example. The electronic device 1001 may provide ultra low-latency services using, e.g., distributed computing or mobile edge computing. In another embodiment, the external electronic device 1004 may include an internet-of-things (IoT) device. The server 1008 may be an intelligent server using machine learning and/or a neural network. According to an embodiment, the external electronic device 1004 or the server 1008 may be included in the second network 1099. The electronic device 1001 may be applied to intelligent services (e.g., smart home, smart city, smart car, or healthcare) based on 5G communication technology or IoT-related technology.

The electronic device according to various embodiments may be one of various types of electronic devices. The electronic devices may include, for example, a portable communication device (e.g., a smartphone), a computer device, a portable multimedia device, a portable medical device, a camera, a wearable device, or a home appliance. According to an embodiment of the disclosure, the electronic devices are not limited to those described above.

It should be appreciated that various embodiments of the disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. As used herein, each of such phrases as "A or B," "at least one of A and B," "at least one of A or B," "A, B, or C," "at least one of A, B, and C," and "at least one of A, B, or C," may include any one of, or all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively," as "coupled with," "coupled to," "connected with," or "connected to" another element (e.g., a second element), it means that the element may be coupled with the other element directly (e.g., wiredly), wirelessly, or via a third element.

As used in connection with various embodiments of the disclosure, the term "module" may include a unit implemented in hardware, software, or firmware, and may interchangeably be used with other terms, for example, "logic," "logic block," "part," or "circuitry." A module may be a single integral component, or a minimum unit or part thereof, adapted to perform one or more functions. For example, according to an embodiment, the module may be implemented in a form of an application-specific integrated circuit (ASIC).

Various embodiments as set forth herein may be implemented as software (e.g., the program 1040) including one or more instructions that are stored in a storage medium (e.g., internal memory 1036 or external memory 1038) that is readable by a machine (e.g., the electronic device 1001). For example, a processor (e.g., the processor 1020) of the machine (e.g., the electronic device 1001) may invoke at least one of the one or more instructions stored in the storage medium, and execute it, with or without using one or more other components under the control of the processor. This allows the machine to be operated to perform at least one function according to the at least one instruction invoked. The one or more instructions may include a code generated by a complier or a code executable by an interpreter. The machine-readable storage medium may be provided in the form of a non-transitory storage medium. Wherein, the term "non-transitory" simply means that the storage medium is a tangible device, and does not include a signal (e.g., an electromagnetic wave), but this term does not differentiate between where data is semi-permanently stored in the storage medium and where the data is temporarily stored in the storage medium.

According to an embodiment, a method according to various embodiments of the disclosure may be included and provided in a computer program product. The computer program product may be traded as a product between a seller and a buyer. The computer program product may be distributed in the form of a machine-readable storage medium (e.g., compact disc read only memory (CD-ROM)), or be distributed (e.g., downloaded or uploaded) online via an application store (e.g., PlayStore™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to various embodiments, each component (e.g., a module or a program) of the above-described components may include a single entity or multiple entities, and some of the multiple entities may be separately disposed in different components. According to various embodiments, one or more of the above-described components may be omitted, or one or more other components may be added. Alternatively or additionally, a plurality of components (e.g., modules or programs) may be integrated into a single component. In such a case, according to various embodiments, the integrated component may still perform one or more functions of each of the plurality of components in the same or similar manner as they are performed by a corresponding one of the plurality of components before the integration. According to various embodiments, operations performed by the module, the program, or another component may be carried out sequentially, in parallel, repeatedly, or heuristically, or one or more of the operations may be executed in a different order or omitted, or one or more other operations may be added.

FIG. 11 is a block diagram of an electronic device for supporting legacy network communication and 5G network communication according to an embodiment of the disclosure.

Referring to FIG. 11, an electronic device 1001 may include a first communication processor (e.g., including processing circuitry) 1112, a second communication processor (e.g., including processing circuitry) 1114, a first radio frequency integrated circuit (RFIC) 1122, a second RFIC 1124, a third RFIC 1126, a fourth RFIC 1128, a first radio frequency front end (RFFE) 1132, a second RFFE 1134, a first antenna module 1142, a second antenna module 1144, and an antenna 1148. The electronic device 1001 may further include a processor (e.g., including processing circuitry) 1020 and a memory 1030. The second network 1099 may include a first cellular network 1192 and a second cellular network 1194. According to another embodiment, the electronic device may further include at least one of the parts shown in FIG. 10 and the second network 1099 may further include at least one another network. According to an embodiment, the first communication processor 1112, the second communication processor 1114, the first RFIC 1122, the second RFIC 1124, the fourth RFIC 1128, the first RFFE 1132, and the second RFFE 1134 may form at least a portion of a wireless communication module 1092. According to another embodiment, the fourth RFIC 1128 may be omitted or may be included as a portion of the third RFIC 1126.

The first communication processor 1112 can support establishment of a communication channel with a band to be used for wireless communication with the first cellular network 1192 and legacy network communication through the established communication channel According to various embodiments, the first cellular network may be a legacy network including a $2^{nd}$ generation (2G), $3^{rd}$ generation (3G), 4G, or Long-Term Evolution (LTE) network. The second communication processor 1114 can support establishment of a communication channel corresponding to a designated band (e.g., about 6 GHz~about 60 GHz) of a band to be used for wireless communication with the second cellular network 1194 and 5G network communication through the established communication channel According to various embodiments, the second cellular network 1194 may be a 5G network that is defined in 3GPP. Further, according to an embodiment, the first communication processor 1112 or the second communication processor 1114 can support establishment of a communication channel corresponding to another designated band (e.g., about 6 GHz or less) of a band to be used for wireless communication with the second cellular network 1194 and 5G network communication through the established communication channel. According to an embodiment, the first communication processor 1112 and the second communication processor 1114 may be implemented in a single chip or a single package. According to various embodiments, the first communication processor 1112 or the second communication processor 1114 may be disposed in a single chip or a single package together with the processor 1020, the auxiliary processor 1023, or the communication module 1090.

The first RFIC 1122, in transmission, can converts a baseband signal generated by the first communication processor 1112 into a radio frequency (RF) signal of about 700 MHz to about 3 GHz that is used for the first cellular network 1192 (e.g., a legacy network). In reception, an RF signal can be obtained from the first cellular network 1192 (e.g., a legacy network) through an antenna (e.g., the first antenna module 1142) and can be preprocessed through an RFFE (e.g., the first RFFE 1132). The first RFIC 1122 can covert the preprocessed RF signal into a baseband signal so that the preprocessed RF signal can be processed by the first communication processor 1112.

The second RFIC 1124 can convert a baseband signal generated by the first communication processor 1112 or the second communication processor 1114 into an RF signal in a Sub6 band (e.g., about 6 GHz or less) (hereafter, 5G Sub6 RF signal) that is used for the second cellular network 1194 (e.g., a 5G network). In reception, a 5G Sub6 RF signal can be obtained from the second cellular network 1194 (e.g., a 5G network) through an antenna (e.g., the second antenna module 1144) and can be preprocessed through an RFFE (e.g., the second RFFE 1134). The second RFIC 1124 can convert the processed 5G Sub6 RF signal into a baseband signal so that the processed 5G Sub6 RF signal can be processed by a corresponding communication processor of the first communication processor 1112 or the second communication processor 1114.

The third RFIC 1126 can convert a baseband signal generated by the second communication processor 1114 into an RF signal in a 5G Above6 band (e.g., about 6 GHz~about 60 GHz) (hereafter, 5G Above6 RF signal) that is used for the second cellular network 1194 (e.g., a 5G network). In reception, a 5G Above6 RF signal can be obtained from the second cellular network 1194 (e.g., a 5G network) through an antenna (e.g., the antenna 1148) and can be preprocessed through the third RFFE 1136. The third RFIC 1126 can covert the preprocessed 5G Above6 RF signal into a baseband signal so that the preprocessed 5G Above6 RF signal can be processed by the first communication processor 1114. According to an embodiment, the third RFFE 1136 may be provided as a portion of the third RFIC 1126.

The electronic device 1001, according to an embodiment, may include a fourth RFIC 1128 separately from or as at least a portion of the third RFIC 1126. In this case, the fourth RFIC 1128 can convert a baseband signal generated by the second communication processor 1114 into an RF signal in an intermediate frequency band (e.g., about 9 GHz~about 11 GHz) (hereafter, IF signal), and then transmit the IF signal to the third RFIC 1126. The third RFIC 1126 can convert the IF signal into a 5G Above6 RF signal. In reception, a 5G Above6 RF signal can be received from the second cellular network 1194 (e.g., a 5G network) through an antenna (e.g., the antenna 1148) and can be converted into an IF signal by the third RFIC 1126. The fourth RFIC 1128 can covert the IF signal into a baseband signal so that IF signal can be processed by the second communication processor 1114.

According to an embodiment, the first RFIC 1122 and the second RFIC 1124 may be implemented as at least a portion of a single chip or a single package. According to an embodiment, the first RFFE 1132 and the second RFFE 1134 may be implemented as at least a portion of a single chip or a single package. According to an embodiment, at least one of the first antenna module 1142 or the second antenna module 1144 may be omitted, or may be combined with another antenna module and can process RF signals in a plurality of bands.

According to an embodiment, the third RFIC 1126 and the antenna 1148 may be disposed on a substrate, thereby being able to form a third antenna module 1146. For example, the wireless communication module 1092 or the processor 1020 may be disposed on a first substrate (e.g., a main PCB). In this case, the third RFIC 1126 may be disposed in a partial area (e.g., the bottom) and the antenna 1148 may be disposed in another partial area (e.g., the top) of a second substrate (e.g., a sub PCB) that is different from the first substrate, thereby being able to form the third antenna module 1146. By disposing the third RFIC 1126 and the antenna 1148 on the same substrate, it is possible to reduce the length of the transmission line therebetween. Accordingly, it is possible to reduce a loss (e.g., attenuation) of a signal in a high-frequency band (e.g., about 6 GHz~about 60 GHz), for example, which is used for 5G network communication, due to a transmission line. Accordingly, the electronic device 1001 can improve the quality and the speed of communication with the second cellular network 1194 (e.g., 5G network).

According to an embodiment, the antenna 1148 may be an antenna array including a plurality of antenna elements that can be used for beamforming. In this case, the third RFIC 1126, for example, as a portion of the third RFFE 1136, may include a plurality of phase shifters 1138 corresponding to the antenna elements. In transmission, the phase shifters 1138 can convert the phase of a 5G Above6 RF signal to be transmitted to the outside of the electronic device 1001 (e.g., to a base station of a 5G network) through the respectively corresponding antenna elements. In reception, the phase shifters 1138 can convert the phase of a 5G Above6 RF signal received from the outside through the respectively corresponding antenna element into the same or substantially the same phase. This enables transmission or reception through beamforming between the electronic device 1001 and the outside.

The second cellular network 1194 (e.g., a 5G network) may be operated independently from (e.g., Stand-Along (SA)) or connected and operated with (e.g., Non-Stand Along (NSA)) the first cellular network 1192 (e.g., a legacy network). For example, there may be only an access network (e.g., a 5G radio access network (RAN) or a next generation RAN (NG RAN)) and there is no core network (e.g., a next generation core (NGC)) in a 5G network. In this case, the electronic device 1001 can access the access network of the 5G network and then can access an external network (e.g., the internet) under control by the core network (e.g., an evolved packed core (EPC)) of the legacy network. Protocol information (e.g., LTE protocol information) for communication with a legacy network or protocol information (e.g., New Radio (NR) protocol information) for communication with a 5G network may be stored in the memory 1130 and accessed by another part (e.g., the processor 1020, the first communication processor 1112, or the second communication processor 1114).

A wearable device 100 according to an embodiment may include: a housing 110 including a first surface, a second surface facing a direction opposite to the first surface, and a lateral surface 110C surrounding a space between the first surface and the second surface; a first input member 103 disposed on the lateral surface 110C of the housing 110 and including a first outer lateral surface 410 including a first conductive portion 411 and at least one first non-conductive portion 412; a first metal member 451 disposed inside the housing 110 and in contact with at least a portion of the first conductive portion 411 of the first outer lateral surface 410; a first printed circuit board (PCB) 431 disposed on the first metal member 451; a first antenna array including at least one conductive patch disposed on a first surface of the first PCB 431 facing the first input member 103 to be arranged at a location corresponding to the at least one first non-conductive portion 412; a wireless communication circuit 470 electrically connected to the first PCB 431 and the first antenna array; and at least one processor electrically connected to the first metal member 451, wherein the wireless communication circuit 470 transmits a signal of a first frequency band by feeding power to the first antenna array, and the at least one processor acquires user biometric information through the first metal member 451 and the first conductive portion 411 of the first input member 103.

According to an embodiment, the wearable device 100 may further include: a second input member 104 disposed on the lateral surface 110C of the housing 110 to be spaced apart from the first input member 103 and including a second outer lateral surface 420 including a second conductive portion 421 and at least one second non-conductive portion 422; a second metal member 452 disposed to be in contact with at least a portion of the second conductive portion 421; a second PCB 432 disposed on the second metal member 452; and a second antenna array including at least one conductive patch disposed on a third surface of the second PCB 432 facing the second input member 104 to be arranged at a location corresponding to the at least one second non-conductive portion 422, wherein the wireless communication circuit 470 is electrically connected to the second PCB 432 and the second antenna array, and feeds power to at least a portion of the first antenna array or the second antenna array to transmit a signal of the first frequency band.

According to an embodiment, the wearable device 100 may further include: at least one third non-conductive portion disposed on the lateral surface 110C of the housing 110; a third PCB disposed inside the housing 110; and a third antenna array including at least one conductive patch disposed in a region of the third PCB corresponding to the at least one third non-conductive portion, wherein the wireless communication circuit 470 is electrically connected to the third PCB and the third antenna array, and feeds power to at least a portion among the first antenna array, the second antenna array, or the third antenna array to transmit a signal of the first frequency band.

According to an embodiment, the first metal member 451 may include at least one first recess 490 formed on one surface thereof facing the first input member 103, and the first PCB 431 may be disposed in the at least one first recess 490 of the first metal member 451.

According to an embodiment, the second metal member 452 may include at least one second recess formed on one surface thereof facing the second input member 104, and the second PCB 432 may be disposed in the at least one second recess of the second metal member 452.

According to an embodiment, the first PCB 431 may further include a fourth antenna array including a dielectric layer disposed on the first antenna array and at least one conductive patch disposed on the dielectric layer, and the wireless communication circuit 470 may be electrically connected to the fourth antenna array to feed power to the fourth antenna array so as to transmit a signal of a second frequency band distinguished from the first frequency band.

According to an embodiment, the fourth antenna array may have a smaller area than the first antenna array.

According to an embodiment, the first frequency band may include a 28 GHz band, and the second frequency band may include a 60 GHz band.

According to an embodiment, the wireless communication circuit 470 may be electrically connected to at least a portion of the housing 110, and feed power to at least a portion of the housing 110 to transmit a signal of a third frequency band distinguished from the first frequency band.

According to an embodiment, the wearable device 100 may include a support member disposed inside the housing 110 and a conductive pattern formed on one surface of the support member, wherein wireless communication circuit 470 is electrically connected to the conductive pattern to feed power to the conductive pattern so as to transmit a signal of a fourth frequency band distinguished from the first frequency band.

According to an embodiment, the signal of the third frequency band may support long-term evolution (LTE) communication, and the signal of the fourth frequency band may support Bluetooth (BT) communication.

The housing 110 according to an embodiment may include an opening formed through the lateral surface 110C, and at least a portion of the first input member 103 may be referred to as a button to be inserted into the opening.

The wireless communication circuit 470 according to an embodiment may include a radio frequency integrated circuit (RFIC) and a power management integrated circuit (PMIC), and may be electrically connected to at least one among the first PCB 431, the second PCB 432, and the third PCB through a conductive connection member 495.

According to an embodiment, the user biometric information may be referred to as at least one of bioelectrical impedance analysis (BIA) and electrocardiogram (ECG).

According to an embodiment, the wearable device 100 may further include binding members 150 and 160 each connected to at least a portion of the housing 110 and configured to enable the housing 110 to be attachable to or detachable from a part of the user's body.

An electronic device 100 according to an embodiment may include: a housing 110 including a first surface, a second surface facing a direction opposite to the first surface, and a lateral surface 110C surrounding a space between the first surface and the second surface; a first input member 103 disposed on the lateral surface 110C of the housing 110 and including a first outer lateral surface 410 including a first conductive portion 411 and at least one first non-conductive portion 412; a second input member 104 disposed on the lateral surface 110C of the housing 110 to be spaced apart from the first input member 103 and including a second outer lateral surface 420 including a second conductive portion 421 and at least one second non-conductive portion 422; a first PCB 431 disposed inside the housing 110 to face the first outer lateral surface 410; a second PCB 432 disposed inside the housing 110 to face the second outer lateral surface 420; at least one first conductive patch disposed on a first surface of the first PCB 431 facing the at least one first non-conductive portion 412 of the first outer lateral surface 410; at least one second conductive patch disposed on a second surface of the second PCB 432 facing the at least one second non-conductive portion 422 of the second outer lateral surface 420; and a wireless communication circuit 470 electrically connected to the first PCB 431 and the second PCB 432, wherein the wireless communication circuit 470 transmits a signal of a first frequency band by feeding power to at least a portion of the at least one first conductive patch or the at least one second conductive patch.

According to an embodiment, the electronic device 100 may further include: a metal member disposed inside the housing 110 and in contact with at least a portion of each of the first conductive portion 411 of the first outer lateral surface 410 and the second conductive portion 421 of the second outer lateral surface 420; and at least one processor electrically connected to the metal member, wherein the at least one processor acquires user biometric information through the metal member and at least one of the first input member 103 and the second input member 104.

According to an embodiment, the electronic device 100 may further include a third PCB disposed inside the housing 110 and at least one third conductive patch disposed on one surface of the third PCB facing the lateral surface 110C of the housing 110, wherein the wireless communication circuit 470 is electrically connected to the at least one third antenna array to feed power to the at least one third conductive patch so as to transmit a signal of the first frequency band.

According to an embodiment, the signal of the first frequency band may include a signal of the mmWave band.

According to an embodiment, the first PCB 431 may further include a dielectric layer disposed on the at least one first conductive patch and at least one fourth conductive patch disposed on the dielectric layer, and the wireless communication circuit 470 may be electrically connected to the at least one fourth antenna array to feed power to the at least one fourth conductive patch so as to transmit a signal of a second frequency band distinguished from the first frequency band.

While the disclosure has been shown and described with reference to various embodiments thereof, it will be understood by those skilled in the art that various changes in form and details may be made therein without departing from the spirit and scope of the disclosure as defined by the appended claims and their equivalents.

What is claimed is:
1. A wearable device comprising:
  a housing comprising a first surface, a second surface facing a direction opposite to the first surface, and a lateral surface surrounding a space between the first surface and the second surface;
  a first input member disposed on the lateral surface of the housing and comprising a first outer lateral surface exposed out of the lateral surface of the housing, the first outer lateral surface of the first input member comprising a first conductive portion and at least one first non-conductive portion;
  a first metal member disposed inside the housing and in contact with at least a portion of the first conductive portion;
  a first printed circuit board (PCB) disposed between the first metal member and the first outer lateral surface;
  a first antenna array comprising at least one first conductive patch disposed on a first PCB surface of the first PCB at a location corresponding to the at least one first non-conductive portion, wherein the first PCB surface of the first PCB faces the first outer lateral surface;
  a wireless communication circuit electrically connected to the first PCB and the first antenna array; and
  at least one processor electrically connected to the first metal member,
  wherein the wireless communication circuit is configured to transmit a signal of a first frequency band by feeding power to the first antenna array, and wherein the at least one processor is configured to acquire user biometric information through the first metal member and the first conductive portion of the first input member.

2. The wearable device of claim 1, further comprising:
a second input member disposed on the lateral surface of the housing and spaced apart from the first input member, and comprising a second outer lateral surface exposed out of the lateral surface of the housing, the second outer lateral surface of the second input member comprising a second conductive portion and at least one second non-conductive portion;
a second metal member disposed to be in contact with at least a portion of the second conductive portion;
a second PCB disposed between the second metal member and the second outer lateral surface; and
a second antenna array comprising at least one second conductive patch disposed on a second PCB surface of the second PCB at a location corresponding to the at least one second non-conductive portion, wherein the second PCB surface of the second PCB faces the second outer lateral surface,
wherein the wireless communication circuit is electrically connected to the second PCB and the second antenna array, and is further configured to transmit a signal of the first frequency band by feeding power to at least a portion of the first antenna array or the second antenna array.

3. The wearable device of claim 2, further comprising:
at least one third non-conductive portion disposed on the lateral surface of the housing;
a third PCB disposed inside the housing; and
a third antenna array comprising at least one third conductive patch disposed in a region of the third PCB corresponding to the at least one third non-conductive portion,
wherein the wireless communication circuit is electrically connected to the third PCB and the third antenna array and is further configured to transmit a signal of the first frequency band by feeding power to at least a portion of the first antenna array, the second antenna array, or the third antenna array.

4. The wearable device of claim 3, wherein the wireless communication circuit comprises a radio frequency integrated circuit (RFIC) and a power management integrated circuit (PMIC), and is electrically connected to at least one among the first PCB, the second PCB, or the third PCB through a conductive connection member.

5. The wearable device of claim 2,
wherein the second metal member comprises at least one second recess formed on one surface thereof facing the second input member, and
wherein the second PCB is disposed in the at least one second recess of the second metal member.

6. The wearable device of claim 1,
wherein the first metal member comprises at least one first recess formed on one surface thereof facing the first input member, and
wherein the first PCB is disposed in the at least one first recess of the first metal member.

7. The wearable device of claim 1,
wherein the first PCB further comprises a fourth antenna array comprising a dielectric layer disposed on the first antenna array and at least one conductive patch disposed on the dielectric layer, and
wherein the wireless communication circuit is electrically connected to the fourth antenna array to, by feeding power to the fourth antenna array, transmit a signal of a second frequency band different from the first frequency band.

8. The wearable device of claim 7, wherein the fourth antenna array has a smaller area than the first antenna array.

9. The wearable device of claim 7, wherein the first frequency band comprises a 28 gigahertz (GHz) band, and the second frequency band comprises a 60 GHz band.

10. The wearable device of claim 1, wherein the wireless communication circuit is electrically connected to at least a portion of the housing, and is further configured to, by feeding power to at least a portion of the housing, transmit a signal of a third frequency band distinguished from the first frequency band.

11. The wearable device of claim 10, further comprising a support member disposed inside the housing and a conductive pattern formed on one surface of the support member,
wherein the wireless communication circuit is electrically connected to the conductive pattern to, by feeding power to the conductive pattern, transmit a signal of a fourth frequency band different from the first frequency band.

12. The wearable device of claim 11, wherein the signal of the third frequency band supports long-term evolution (LTE) communication, and the signal of the fourth frequency band supports Bluetooth (BT) communication.

13. The wearable device of claim 1,
wherein the housing comprises an opening formed through the lateral surface thereof, and
wherein at least a portion of the first input member is configured as a button to be inserted into the opening.

14. The wearable device of claim 1, wherein the user biometric information is at least one of bioelectrical impedance analysis (BIA) or electrocardiogram (ECG).

15. The wearable device of claim 1, further comprising binding members each connected to at least a portion of the housing and configured to enable the housing to be attachable to or detachable from a part of a user's body.

16. An electronic device comprising:
a housing comprising a first surface, a second surface facing a direction opposite to the first surface, and a lateral surface surrounding a space between the first surface and the second surface;
a first input member disposed on the lateral surface of the housing and comprising a first outer lateral surface exposed out of the lateral surface of the housing, the first outer lateral surface of the first input member comprising a first conductive portion and at least one first non-conductive portion;
a second input member disposed on the lateral surface of the housing and spaced apart from the first input member, and comprising a second outer lateral surface exposed out of the lateral surface of the housing, the second outer lateral surface of the second input member comprising a second conductive portion and at least one second non-conductive portion;
a first printed circuit board (PCB) disposed inside the housing to face the first outer lateral surface;
a second PCB disposed inside the housing to face the second outer lateral surface;
at least one first antenna array disposed on a first PCB surface of the first PCB at a location corresponding to the at least one first non-conductive portion, wherein the first PCB surface faces the first outer lateral surface;
at least one second antenna array disposed on a second PCB surface of the second PCB at a location corresponding to the at least one second non-conductive portion, wherein the second PCB surface faces the second outer lateral surface; and a wireless communication circuit electrically connected to the first PCB and the second PCB, wherein the wireless communication circuit is configured to transmit a signal of a first frequency band by feeding power to at least a portion of the at least one first antenna array or the at least one second antenna array.

17. The electronic device of claim 16, further comprising:
a metal member disposed inside the housing and in contact with at least a portion of each of the first conductive portion of the first outer lateral surface and the second conductive portion of the second outer lateral surface; and
at least one processor electrically connected to the metal member,
wherein the at least one processor is configured to acquire user biometric information through the metal member and at least one of the first input member or the second input member.

18. The electronic device of claim 16, further comprising:
a third PCB disposed inside the housing; and
at least one third antenna array disposed on a third surface of the third PCB, the at least one third antenna array facing the lateral surface of the housing,
wherein the wireless communication circuit is electrically connected to the at least one third antenna array to, by feeding power to the at least one third antenna array, transmit a signal of the first frequency band.

19. The electronic device of claim 16, wherein the signal of the first frequency band comprises a signal of a millimeter wave (mmWave) band.

20. The electronic device of claim 16,
wherein the first PCB further comprises:
a dielectric layer disposed on the at least one first antenna array, and
at least one fourth antenna array disposed on the dielectric layer, and
wherein the wireless communication circuit is electrically connected to the at least one fourth antenna array to, by feeding power to the at least one fourth antenna array, transmit a signal of a second frequency band different from the first frequency band.

* * * * *